US010485896B2

(12) United States Patent
Lebreton

(10) Patent No.: US 10,485,896 B2
(45) Date of Patent: *Nov. 26, 2019

(54) HYALURONIC ACID-BASED GELS INCLUDING LIDOCAINE

(71) Applicant: Allergan Industrie SAS, Pringy (FR)

(72) Inventor: Pierre F. Lebreton, Annecy (FR)

(73) Assignee: ALLERGAN INDUSTRIE SAS, Pringy (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/186,448

(22) Filed: Nov. 9, 2018

(65) Prior Publication Data
US 2019/0076579 A1 Mar. 14, 2019

Related U.S. Application Data

(63) Continuation of application No. 15/443,080, filed on Feb. 27, 2017, which is a continuation of application No. 14/754,504, filed on Jun. 29, 2015, now abandoned, which is a continuation of application No. 14/242,752, filed on Apr. 1, 2014, now abandoned, which is a continuation of application No. 13/419,079, filed on Mar. 13, 2012, now Pat. No. 8,822,676, which is a continuation of application No. 12/393,884, filed on Feb. 26, 2009, now Pat. No. 8,357,795.

(60) Provisional application No. 61/085,956, filed on Aug. 4, 2008, provisional application No. 61/087,934, filed on Aug. 11, 2008, provisional application No. 61/096,278, filed on Sep. 11, 2008.

(51) Int. Cl.
A61L 27/52 (2006.01)
A61K 8/42 (2006.01)
A61K 8/73 (2006.01)
A61L 27/20 (2006.01)
A61L 27/54 (2006.01)
A61Q 19/08 (2006.01)
A61K 31/167 (2006.01)
A61K 31/728 (2006.01)
A61K 9/00 (2006.01)
A61K 9/06 (2006.01)
A61K 47/36 (2006.01)

(52) U.S. Cl.
CPC .............. *A61L 27/52* (2013.01); *A61K 8/42* (2013.01); *A61K 8/735* (2013.01); *A61K 9/0021* (2013.01); *A61K 9/06* (2013.01); *A61K 31/167* (2013.01); *A61K 31/728* (2013.01); *A61K 47/36* (2013.01); *A61L 27/20* (2013.01); *A61L 27/54* (2013.01); *A61Q 19/08* (2013.01); A61L 2300/402 (2013.01); A61L 2300/602 (2013.01); A61L 2400/06 (2013.01)

(58) Field of Classification Search
CPC .......... A61K 8/42; A61K 8/735; A61K 9/002; A61K 9/06; A61K 31/167; A61K 31/728; A61L 27/52; A61L 27/20; A61L 27/54; A61L 2300/402; A61L 2300/602; A61L 2400/06; A61Q 19/08
See application file for complete search history.

(56) References Cited

U.S. PATENT DOCUMENTS

| 2,128,827 | A | 8/1938 | Killian |
| 3,548,056 | A | 12/1970 | Eigen et al. |
| 3,763,009 | A | 10/1973 | Suzuki |
| 3,949,073 | A | 4/1976 | Daniels et al. |
| 4,060,081 | A | 11/1977 | Yannas et al. |
| 4,140,537 | A | 2/1979 | Luck et al. |
| 4,233,360 | A | 11/1980 | Luck et al. |
| 4,273,705 | A | 6/1981 | Kato |
| 4,279,812 | A | 7/1981 | Cioca |
| 4,424,208 | A | 1/1984 | Wallace et al. |
| 4,501,306 | A | 2/1985 | Chu et al. |
| 4,582,640 | A | 4/1986 | Smestad et al. |
| 4,582,865 | A | 4/1986 | Balazs et al. |
| 4,605,691 | A | 8/1986 | Balazs et al. |
| 4,636,524 | A | 1/1987 | Balazs |
| 4,642,117 | A | 2/1987 | Nguyen et al. |

(Continued)

FOREIGN PATENT DOCUMENTS

| CA | 949965 | 6/1974 |
| CA | 2416504 | 1/2002 |

(Continued)

OTHER PUBLICATIONS

British Pharmacopoeia Lidocaine Safety Data Sheet according to 1907/2006/EC, Article 31 printed Nov. 22, 2013.

(Continued)

*Primary Examiner* — Ali Soroush

(74) *Attorney, Agent, or Firm* — Nathan S. Smith; Morgan, Lewis & Bockius LLP

(57) ABSTRACT

Disclosed herein are cohesive soft tissue fillers, for example, dermal and subdermal fillers, based on hyaluronic acids and pharmaceutically acceptable salts thereof. In one aspect, hyaluronic acid-based compositions described herein include a therapeutically effective amount of at least one anesthetic agent, for example, lidocaine. The present hyaluronic acid-based compositions including lidocaine have an enhanced stability and cohesivity, relative to conventional compositions including lidocaine, for example when subjected to sterilization techniques or when stored for long periods of time. Methods and processes of preparing such hyaluronic acid-based compositions are also provided.

30 Claims, 5 Drawing Sheets

(56) References Cited

U.S. PATENT DOCUMENTS

| | | |
|---|---|---|
| 4,713,448 A | 12/1987 | Balazs |
| 4,716,154 A | 12/1987 | Malson et al. |
| 4,772,419 A | 9/1988 | Malson et al. |
| 4,803,075 A | 2/1989 | Wallace et al. |
| 4,886,787 A | 12/1989 | De Belder et al. |
| 4,896,787 A | 1/1990 | Delamour et al. |
| 5,009,013 A | 4/1991 | Wiklund |
| 5,079,236 A | 1/1992 | Drizen et al. |
| 5,087,446 A | 2/1992 | Suzki et al. |
| 5,091,171 A | 2/1992 | Yu et al. |
| 5,143,724 A | 9/1992 | Leshchiner et al. |
| 5,246,698 A | 9/1993 | Leshchiner et al. |
| 5,314,874 A | 5/1994 | Miyata et al. |
| 5,328,955 A | 7/1994 | Rhee et al. |
| 5,356,883 A | 10/1994 | Kuo et al. |
| 5,399,351 A | 3/1995 | Leshchiner et al. |
| 5,428,024 A | 6/1995 | Chu et al. |
| 5,531,716 A | 7/1996 | Luzio et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamoto |
| 5,616,689 A | 4/1997 | Shenoy et al. |
| 5,633,001 A | 5/1997 | Agerup |
| 5,643,464 A | 7/1997 | Rhee et al. |
| 5,676,964 A | 10/1997 | della Valle |
| 5,731,298 A | 3/1998 | Reinmuller |
| 5,823,671 A | 10/1998 | Mitchell et al. |
| 5,824,333 A | 10/1998 | Scopelianos et al. |
| 5,827,529 A | 10/1998 | Ono et al. |
| 5,843,907 A | 12/1998 | Sakai |
| 5,880,107 A | 3/1999 | Buenter |
| 5,886,042 A | 3/1999 | Yu et al. |
| 5,935,164 A | 8/1999 | Iversen |
| 5,972,326 A | 10/1999 | Galin et al. |
| 5,980,930 A | 11/1999 | Fenton et al. |
| 6,013,679 A | 1/2000 | Kuo et al. |
| 6,066,325 A | 5/2000 | Wallace et al. |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci |
| 6,767,924 B2 | 7/2004 | Yu et al. |
| 6,767,928 B1 | 7/2004 | Murphy et al. |
| 6,852,255 B2 | 2/2005 | Yang |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,119,062 B1 | 10/2006 | Alvis et al. |
| 7,166,570 B2 | 1/2007 | Hunter et al. |
| 7,192,984 B2 | 3/2007 | Berg |
| 7,196,180 B2 | 3/2007 | Aeschlimann |
| 7,314,636 B2 | 1/2008 | Caseres et al. |
| 7,491,709 B2 | 2/2009 | Carey |
| 7,741,476 B2 | 6/2010 | Lebreton |
| 7,902,171 B2 | 3/2011 | Reinmuller |
| 8,052,990 B2 | 11/2011 | Hermitte et al. |
| 8,124,120 B2 | 2/2012 | Sadozai |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 * | 1/2013 | Lebreton ................ A61K 8/42 536/124 |
| 8,394,782 B2 | 3/2013 | Stroumpoulis et al. |
| 8,394,783 B2 * | 3/2013 | Stroumpoulis ........ A61K 8/042 514/54 |
| 8,394,784 B2 * | 3/2013 | Stroumpoulis ........ A61K 8/042 514/55 |
| 8,450,475 B2 * | 5/2013 | Lebreton ................ A61K 8/42 536/124 |
| 8,455,465 B2 | 6/2013 | Molliard |
| 8,513,216 B2 | 8/2013 | Stroumpoulis et al. |
| 8,524,213 B2 | 9/2013 | Leshchiner et al. |
| 8,563,532 B2 | 10/2013 | Lebreton |
| 8,575,129 B2 | 11/2013 | Bellini |
| 8,586,562 B2 | 11/2013 | Lebreton |
| 8,657,795 B2 | 2/2014 | Magalich et al. |
| 8,822,676 B2 * | 9/2014 | Lebreton ................ A61K 8/42 536/124 |
| 9,089,517 B2 * | 7/2015 | Lebreton ................ A61K 8/42 |
| 9,089,518 B2 * | 7/2015 | Lebreton ................ A61K 8/42 |
| 9,089,519 B2 * | 7/2015 | Lebreton ................ A61K 8/42 |
| 9,114,188 B2 * | 8/2015 | Gousse ................ A61L 27/20 |
| 9,238,013 B2 * | 1/2016 | Lebreton ................ A61K 8/42 |
| 9,358,322 B2 * | 6/2016 | Lebreton ................ A61K 8/42 |
| 9,393,263 B2 * | 7/2016 | Liu ...................... A61K 31/728 |
| 2002/0019339 A1 | 2/2002 | Naughton et al. |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter |
| 2005/0186261 A1 | 8/2005 | Avelar |
| 2005/0186673 A1 | 8/2005 | Geistlich et al. |
| 2005/0226936 A1 | 10/2005 | Agerup |
| 2005/0250939 A1 | 11/2005 | Zhao |
| 2005/0271729 A1 | 12/2005 | Wang |
| 2005/0281880 A1 | 12/2005 | Wang |
| 2005/0287180 A1 | 12/2005 | Chen |
| 2006/0040894 A1 | 2/2006 | Hunter et al. |
| 2006/0058238 A1 | 3/2006 | Laurent-Applegate et al. |
| 2006/0095137 A1 | 5/2006 | Chung et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0189516 A1 | 8/2006 | Yang |
| 2006/0194758 A1 | 8/2006 | Lebreton |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0026070 A1 | 2/2007 | Vonwiller et al. |
| 2007/0066816 A1 | 3/2007 | Tsai et al. |
| 2007/0077292 A1 | 4/2007 | Pinsky |
| 2007/0184087 A1 | 8/2007 | Voigts |
| 2007/0203095 A1 | 8/2007 | Sadozai et al. |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui |
| 2008/0089918 A1 | 4/2008 | Lebreton |
| 2008/0188416 A1 | 8/2008 | Bernstein |
| 2008/0188441 A1 | 8/2008 | Reinmuller |
| 2008/0193538 A1 | 8/2008 | Kitazono et al. |
| 2008/0200430 A1 | 8/2008 | Bitterman et al. |
| 2008/0207794 A1 | 8/2008 | Wright et al. |
| 2008/0226724 A1 | 9/2008 | Ji et al. |
| 2008/0241252 A1 | 10/2008 | Lyons |

(56) References Cited

U.S. PATENT DOCUMENTS

| | | |
|---|---|---|
| 2008/0268051 A1 | 10/2008 | Lyons |
| 2008/0274946 A1 | 11/2008 | Gimpapa |
| 2008/0279806 A1 | 11/2008 | Cho |
| 2008/0293637 A1 | 11/2008 | Schroeder et al. |
| 2009/0017091 A1 | 1/2009 | Daniloff et al. |
| 2009/0018102 A1 | 1/2009 | Moutet |
| 2009/0022808 A1 | 1/2009 | Championn |
| 2009/0028817 A1 | 1/2009 | Niklason et al. |
| 2009/0035251 A1 | 2/2009 | Wortzman et al. |
| 2009/0036403 A1 | 2/2009 | Stroumpoulis et al. |
| 2009/0042834 A1 | 2/2009 | Karageozian et al. |
| 2009/0093755 A1 | 4/2009 | Schroeder |
| 2009/0110671 A1 | 4/2009 | Miyata et al. |
| 2009/0110736 A1 | 4/2009 | Boutros |
| 2009/0143331 A1 | 6/2009 | Stroumpoulis et al. |
| 2009/0143348 A1 | 6/2009 | Tezel |
| 2009/0148527 A1 | 6/2009 | Robinson |
| 2009/0155314 A1 | 6/2009 | Tezel |
| 2009/0155362 A1 | 6/2009 | Longin |
| 2009/0169615 A1 | 7/2009 | Pinsky |
| 2009/0263447 A1 | 10/2009 | Asius et al. |
| 2009/0291986 A1 | 11/2009 | Pappas et al. |
| 2009/0297632 A1 | 12/2009 | Waugh |
| 2010/0004198 A1 | 1/2010 | Stroumpoulis et al. |
| 2010/0028437 A1 | 2/2010 | Lebreton |
| 2010/0028438 A1 | 2/2010 | Lebreton |
| 2010/0035838 A1 | 2/2010 | Herber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0226988 A1 | 9/2010 | Lebreton |
| 2010/0255068 A1 | 10/2010 | Stroumpoulis et al. |
| 2010/0316683 A1 | 12/2010 | Piron et al. |
| 2011/0034684 A1 | 2/2011 | Yokokawa |
| 2011/0077737 A1 | 3/2011 | Stroumpoulis et al. |
| 2011/0118206 A1 | 5/2011 | Lebreton |
| 2011/0171286 A1 | 7/2011 | Cecile et al. |
| 2011/0171311 A1 | 7/2011 | Gousse et al. |
| 2011/0172180 A1 | 7/2011 | Gousse et al. |
| 2011/0224164 A1 | 9/2011 | Lebreton |
| 2011/0229574 A1 | 9/2011 | Guillen et al. |
| 2012/0010146 A1 | 1/2012 | Han et al. |
| 2012/0018959 A1 | 1/2012 | Anderson et al. |
| 2012/0034462 A1 | 2/2012 | Stroumpoulis et al. |
| 2012/0071437 A1 | 3/2012 | Stroumpoulis et al. |
| 2012/0095206 A1 | 4/2012 | Chen |
| 2012/0100217 A1 | 4/2012 | Green |
| 2012/0142628 A1 | 6/2012 | Lalwani |
| 2012/0164098 A1 | 6/2012 | Schroeder et al. |
| 2012/0172328 A1 | 7/2012 | Lebreton |
| 2012/0189589 A1 | 7/2012 | Van Epps et al. |
| 2012/0189590 A1 | 7/2012 | Van Epps et al. |
| 2012/0189591 A1 | 7/2012 | Van Epps et al. |
| 2012/0189699 A1 | 7/2012 | Stroumpoulis et al. |
| 2012/0189708 A1 | 7/2012 | Van Epps et al. |
| 2012/0190644 A1 | 7/2012 | D'este et al. |
| 2012/0208890 A1 | 8/2012 | Gousse et al. |
| 2012/0225842 A1 | 9/2012 | Cecile et al. |
| 2012/0232030 A1 | 9/2012 | Gousse et al. |
| 2012/0295870 A1 | 11/2012 | Lebreton |
| 2013/0023658 A1 | 1/2013 | Stroumpoulis et al. |
| 2013/0041038 A1 | 2/2013 | Lebreton |
| 2013/0041039 A1 | 2/2013 | Lebreton |
| 2013/0072453 A1 | 3/2013 | Gousse et al. |
| 2013/0096081 A1 | 4/2013 | Njikang |
| 2013/0102563 A1 | 4/2013 | Lebreton |
| 2013/0116188 A1 | 5/2013 | Pollock et al. |
| 2013/0116190 A1 | 5/2013 | Pollock et al. |
| 2013/0116411 A1 | 5/2013 | Pollock et al. |
| 2013/0123210 A1 | 5/2013 | Liu |
| 2013/0131011 A1 | 5/2013 | Lebreton |
| 2013/0136780 A1 | 5/2013 | Tezel et al. |
| 2013/0203696 A1 | 8/2013 | Liu |
| 2013/0209532 A1 | 8/2013 | Stroumpoulis et al. |
| 2013/0210760 A1 | 8/2013 | Liu |
| 2013/0237615 A1 | 9/2013 | Meunier |
| 2013/0244943 A1 | 9/2013 | Yu et al. |
| 2013/0244970 A1 | 9/2013 | Lebreton |
| 2013/0274222 A1 | 10/2013 | Horne |
| 2014/0011980 A1 | 1/2014 | Chitre et al. |
| 2014/0011990 A1 | 1/2014 | Lebreton |
| 2016/0279296 A1* | 9/2016 | Lebreton .................. A61K 8/42 |
| 2018/0000992 A1* | 1/2018 | Lebreton .................. A61K 8/42 |

FOREIGN PATENT DOCUMENTS

| | | |
|---|---|---|
| EP | 273823 | 7/1988 |
| EP | 416250 | 3/1991 |
| EP | 416846 | 3/1991 |
| EP | 839159 | 8/2001 |
| EP | 1247522 | 10/2002 |
| EP | 1419792 | 4/2003 |
| EP | 1398131 | 3/2004 |
| EP | 1532991 | 5/2005 |
| EP | 1726299 | 11/2006 |
| EP | 2236523 | 10/2010 |
| EP | 1303542 | 7/2012 |
| EP | 1701981 | 6/2017 |
| EP | 3205332 | 8/2017 |
| FR | 2733427 | 10/1996 |
| FR | 2920000 | 2/2009 |
| FR | 2924615 | 6/2009 |
| JP | S55-153711 | 11/1980 |
| JP | 2002-080501 | 8/2002 |
| JP | 2007-063177 | 3/2007 |
| JP | 2007-525541 | 9/2007 |
| JP | 2011-529762 | 12/2011 |
| WO | WO 86/00079 | 1/1986 |
| WO | WO 86/00912 | 2/1986 |
| WO | WO 92/00105 | 1/1992 |
| WO | WO 92/20349 | 11/1992 |
| WO | WO 93/12801 | 7/1993 |
| WO | WO 94/01468 | 1/1994 |
| WO | WO 94/02517 | 2/1994 |
| WO | WO 96/33751 | 10/1996 |
| WO | WO 97/04012 | 2/1997 |
| WO | WO 98/35639 | 8/1998 |
| WO | WO 98/35640 | 8/1998 |
| WO | WO 00/01428 | 1/2000 |
| WO | WO 01/60868 | 8/2001 |
| WO | WO 01/79342 | 10/2001 |
| WO | WO 02/05753 | 1/2002 |
| WO | WO 02/06350 | 1/2002 |
| WO | WO 02/09792 | 2/2002 |
| WO | WO 02/17713 | 3/2002 |
| WO | WO 03/007782 | 1/2003 |
| WO | WO 2004/020473 | 3/2004 |
| WO | WO 2004/022603 | 3/2004 |
| WO | WO 2004/032943 | 4/2004 |
| WO | WO 2004/073759 | 9/2004 |
| WO | WO 2004/092222 | 10/2004 |
| WO | WO 2004/092223 | 10/2004 |
| WO | WO 2005/040224 | 5/2005 |
| WO | WO 2005/066215 | 7/2005 |
| WO | WO 2005/067944 | 7/2005 |
| WO | WO 2005/067994 | 7/2005 |
| WO | WO 2005/074913 | 8/2005 |
| WO | WO 2005/112888 | 12/2005 |
| WO | WO 2005/113608 | 12/2005 |
| WO | WO 2006/002365 | 1/2006 |
| WO | WO 2006/023645 | 3/2006 |
| WO | WO 2006/067608 | 6/2006 |
| WO | WO 2006/102676 | 6/2006 |
| WO | WO 2007/018124 | 2/2007 |
| WO | WO 2007/070617 | 6/2007 |
| WO | WO 2007/077399 | 7/2007 |
| WO | WO 2007/128923 | 11/2007 |
| WO | WO 2007/136738 | 11/2007 |
| WO | WO 2008/034176 | 3/2008 |
| WO | WO 2008/068297 | 6/2008 |
| WO | WO 2008/072230 | 6/2008 |

(56) References Cited

FOREIGN PATENT DOCUMENTS

| | | |
|---|---|---|
| WO | WO 2008/077172 | 7/2008 |
| WO | WO 2008/098019 | 8/2008 |
| WO | WO 2008/139122 | 11/2008 |
| WO | WO 2008/148967 | 12/2008 |
| WO | WO 2008/157608 | 12/2008 |
| WO | WO 2009/024719 | 2/2009 |
| WO | WO 2009/026158 | 2/2009 |
| WO | WO 2009/028764 | 3/2009 |
| WO | WO 2009/034559 | 3/2009 |
| WO | WO 2009/073437 | 6/2009 |
| WO | WO 2010/003797 | 1/2010 |
| WO | WO 2010/015900 | 2/2010 |
| WO | WO 2010/015901 | 2/2010 |
| WO | WO 2010/027471 | 3/2010 |
| WO | WO 2010/028025 | 3/2010 |
| WO | WO 2010/029344 | 3/2010 |
| WO | WO 2010/038771 | 4/2010 |
| WO | WO 2010/051641 | 5/2010 |
| WO | WO 2010/052430 | 5/2010 |
| WO | WO 2010/053918 | 5/2010 |
| WO | WO 2010/061005 | 6/2010 |
| WO | WO 2012/077055 | 6/2012 |

OTHER PUBLICATIONS

Brown et al., Hyaluronic acid: A unique topical vehicle for the localized delivery of drugs to the skin,: Journal of the Europan Academy of Dermatology and Venerology, 2005, 308-319, vol. 19.
Budavani et al., The Merck Index, Merck & CO, 1989, Ed 11, p. 5360.
Cosmetic Tissue Augmentation Product (CTA), Summary of Safety and Effectiveness, Dec. 20, 2006, 12 pages.
FDA Advisory Committee Briefing Document, Summary of Safety and Effectiveness Data, Juvederm Voluma XC, 2013, 147 pages (in 5 parts).
Judeverm Ultra label, product information about Juvederm Ultra by Allergan.
Judeverm Ultra Plus label, product information about Juvederm Ultra Plus by Allergan.
Judeverm Ultra Plus XC label, product information about Juvederm Ultra Plus XC by Allergan.
Judeverm Voluma label, product information about Juvederm Voluma by Allergan.
Juvederm Press Release, Jan. 11, 2008, Pharm-Allergan GmBH (German).
Juvederm Ultra Plus XC, Product Information Sheet, Allergan Inc., 2010.
Juvederm Ultra Product Summary, Jul. 2011, www.consultingroom. com, 3 pages.
Juvederm Ultra XC with Lidocaine Granted FDA Approval, The Plastic Surgery Experts at the Mandell Brown Plastic Center Surgery Center, http://www.mandellbrown.com/blog/2010/juvederm-ultra-xc-with lidocaine-granted-fda-approval, Jan. 9, 2013.
Kulicke et al., "Visco-Elastic Properties of Sodium Hyaluronate Solutions," American Institute of Physics (2008).
Kuo, "Practical Aspects of Hyaluronan Based Medical Products," 2006, 34-43, 79-93, CRC Press, Boca Raton FL.
Levy et al., Comparison of Injection Comfort and Ease with Juvederm Ultra 3 and Surgiderm 30 XP, 2008.
Merz Pharmaceuticals GmBH, Test Report Apr. 21, 2017.
Nortier et al., "Preparation and stability of testing of a hydrogel for topical analgesia," Pharmacy World and Science, Nov. 24, 1995, 214-217, vol. 17, Issue 6.
Priority document to Ji, U.S. Appl. No. 60/881,260, filed Jan. 19, 2007.
Priority document to Wortzman, U.S. Appl. No. 60/953,661, filed Aug. 2, 2007.
Selyanin et al., "Hyaluronic Acid Preparation, Properties, Application in Biology and Medicine," John Wiley & Sons, 2015, p. 88.
Summary of Safety and Effectiveness Data of Juvederm 30, 24HV and 30HV, issued Jun. 2, 2006, Updated Jun. 29, 2006, available at https://www.accessdata.fda.gov/cdrh_docs/pdf5/P050047b.pdf.
What is Juvederm XC?, http://www.juvederm.com/views/what-is-juvederm/, Jan. 1, 2013, 2 pages.
EP 2323617 Communication Pursuant to Rule 114(2) EPC Third Party Observations, Oct. 2, 2013, 185 pages.
EP 2326302 Communication pursuant to Rule 114(2) EPC, Third Party Observations, Dec. 23, 2015.
EP Search Report from Application No. 13004017.3, dated Nov. 15, 2013, 8 pages.
EP 2637710 Communication Pursuant to Rule 114(2) EPC Third Party Observations, dated Feb. 1, 2016.
"Claim Construction Order", *Allergan USA, Inc. et al. v. Medicis Aesthetics, Inc., et al.*, Case No. SACV 13/1436 AG (JPRx), United States District Court for the Central District of California, Aug. 12, 2014, 21 Pages.
"Defendants' Answering Claim Construction Brief", *Allergan USA, Inc. et al. v. Medicis Aesthetics, Inc. et al.*, Case No. 8:13-cv-01436 AG (JPRx), United States District Court Central District of California, Jun. 27, 2014. 11 Pages.
"Defendants' Invalidity Contentions", *Allergan USA, Inc. et al. v. Medicis Aesthetics, Inc. et al.*, Case No. 8:13-cv-01436 AG (JPRx), United States District Court Central District of California, Apr. 4, 2014.
"Defendants' Opening Claim Construction Brief", *Allergan USA, Inc. et al. v. Medicis Aesthetics, Inc. et al.*, Case No. 8:13-cv-01436 AG (JPRx), United States District Court Central District of California, Jun. 13, 2014, 23 Pages.
"Plaintiffs' Opening Claim Construction Brief", *Allergan USA, Inc. et al. v. Medicis Aesthetics, Inc. et al.*, Case No. 8:13-cv-01436 AG (JPRx), United States District Court Central District of California, Jul. 22, 2014, 30 Pages.
"Plaintiffs' Responsive Claim Construction Brief", *Allergan USA, Inc. et al. v. Medicis Aesthetics, Inc. et al.*, Case No. 8:13-cv-01436 AG (JPRx), United States District Court Central District of California, Jul. 22, 2014, 14 Pages.
475 Patent Invalidity Claim Charts, 11 Pages, Feb. 17, 2015.
475 Patent Obviousness Claim Chart, 51 Pages, Feb. 17, 2015.
795 Patent Invalidity Claim Charts, 12 Pages, Feb. 17, 2015.
795 Patent Obviousness Claim Charts, 28 Pages, Feb. 17, 2015.
Adams, "An Analysis of Clinical Studies of the Uses of Crosslinked Hyaluronan, Hylan, in the Treatment of Osteoarthritis", J. Rheumatol Suppl., Aug. 1993; 39:16-8.
Aesthetic Buyers Guide, "Juvederm Raises Standards" Jan./Feb. 2007 (5 pp.), www.miinews.com.
Albano, Emanuele, et al., "Hydroxyethyl Radicals in Ethanol Hepatotoxicity," Frontiers in Bioscience 4:533-540 (1999).
Allemann et al., "Hyaluronic acid gel (Juvederm) preparations in the treatment of facial wrinkles and folds", 2008, Clinical Interventions in Aging, vol. 3, No. 4, pp. 629-634.
*Allergan, Inc.v. Medicis Aesthetics, Inc.et al.*, Defendants' Final Invalidity Contentions, 16 Pages, Feb. 17, 2015.
Ambroziak, Marcin, "Volumetry: new opportunities for rejuvenating and modeling of your facial features", Ekspert, Sep./Oct. 2006, pp. 5-6.
Antunes, Alberto A., et al., "Efficacy of Intrarectal Lidocaine Hydrochloride Gel for Pain control in Patients Undergoing Transrectal Prostate Biopsy", International Braz J Urol, vol. 30(5): 380-383, Sep.-Oct. 2004.
Atanassoff, Peter G., et al., "The Effect of Intradermal Administration of Lidocaine and Morphine on the Response to Thermal Stimulation", Anesth Analg 1997; 84:1340-3.
Balazs, E. A. and Band, P. A., Therapeutic Use of Hyaluronan-Based Products, in: Carbohydrate Chemistry, Biology and Medical Applications, Garg, H. G., Cowman, M. K., and Hales, C. A. (Eds.), pp. 311-332, first edition, 2008, Elsevier Ltd.
Ballin, Annelyse et al., Long-Term Efficacy, Safety and Durability of Juvederm XC, Clin Cosmet Investig Dermtol., 6:183-189, Published Online Aug. 2, 2013.
Baumann et al. "Juvederm vs. Zyplast Nasolabial Fold Study Group, Comparison of smooth-gel hyaluronic acid dermal fillers

(56) References Cited

OTHER PUBLICATIONS with cross-linked bovine collagen: a multicenter, double-masked, randomized, within-subject study." Dermatol. Surg. 33(Suppl 2): S128-S135 (2007).
Beasley et al. :Hyaluronic acid fillers: a comprehensive review. Facial Plast. Surg. 25(2): 86-94 (2009).
Beer "Dermal fillers and combinations of fillers for facial rejuvenation." Dermatol. Clin. 27(4): 427-432 (2009).
Belda, Jose I., et al., "Hyaluronic acid combined with mannitol to improve protection against free-radical endothelial damage: Experimental Model," J.Cataract Refract Surg 2005; 31:1213-1218.
Bircher, Andreas J., et al., "Delayed-type hypersensitivity to subcutaneous lidocaine with tolerance to articaine: confirmation by in vivo and in vitro tests", Contact Dermatitis 1996, 34, 387-389.
Bloomberg News. "Mentor Corporation Announces FDA Approval of Prevelle Silk", http://www.bloomberg.com/apps/news?pid=newsarchive&sid=arVm09DtIA5- c, Mar. 21, 2008.
Bluel et al., "Evaluation of Reconstituted Collagen Tape as a Model for Chemically Modified Soft Tissues", Biomat. Med. De. Art. Org., 9(1):37-46 (1981).
Borrell, Marcos et al., Life Capabilities of Hyaluronic Acid Fillers, J. Cosmetic and Laser Therapy, 13:21-27 (2011).
Boulle et al., "Lip Augmentation and Contour Correction With a Ribose Cross-linked Collagen Dermal Filler", Journals of Drugs in Dermatology, Mar. 2009, vol. 8, Issue 3, pp. 1-8.
British Pharmacopoeia, Monograph on Lidocaine Hydrochloride, 4 Pages, 2012.
Bruskov et al., "Heat-Induced Generation of Reactive Oxygen Species during Reduction of Dissolved Air Oxygen", Doklady Akademii Nauk, 381(2): 262-264, 2001.
Buck et al, "Injectable Fillers for our Facial Rejuvenation: a Review", Journal of Plastic, Reconstructive and Aesthetic Surgery, (2009), 62:11-18, XP002668828.
Capozzi et al., "Distant Migration of Silicone Gel From a Ruptured Breats Implant", Plastic and Reconstructive Surgery, 1978; 62:302-3.
Carlin, G., et al., "Effect of anti-inflammatory drugs on xanthine oxidase and xanthine oxidase induced depolymerization of hyaluronic acid," Agents and Actions. 16 (5):377-384 (1985).
Carruthers et al. "The science and art of dermal fillers for soft-tissue augmentation." J. Drugs Dermatol. 8(4):335-350 (2009).
Champion, et al., "Role of Target Geometry in Phagocytosis", S. Proc. Nat. Acad. Sci., Mar. 2008, 2006, vol. 103, No. 13, pp. 4930-4934.
Chin, Thomas M., et al., "Allergic Hypersensitivity to Lidocaine Hydrochloride", International journal of Dermatology, vol. 19, Apr. 1980, pp. 147-148.
Chvapil, "Collagen Sponse: Theory and Practice of Medical Applications", J. Biomed Mater. Res., II, pp. 721-741 (1977).
Clark et al., "The Influence of Triamcinolone Acetonide on Joint Stiffness in the Rat", J Bone Joint Surg Am, 1971; 53:1409-1414.
Cohen et al., "Organization and Adhesive Properties of the Hyaluronan Pericellular Coat of Chondrocytes and Epithelial Cells", Biophys J., 2003; 85:1996-2005.
Crosslinking Technical Handbook, Thermo Scientific, pp. 1-48, published Apr. 2009.
Cui et al; "The Comparison of Physicochemical Properties of Four Cross-Linked Sodium Hyaluronate Gels with Different Cross-Linking Agents"; Advanced Material Research; vols. 396-398; pp. 1506-1512; 2012.
Das et al., "Lidocaine: a hydroxyl radical scavenger and singlet oxygen quencher", Molecular and Cellular Biochemistry 115:179-185, 1992.
Declaration of Dr. Glenn Prestwich in Support of this IPR Petition, 107 Pages, Apr. 17, 2014.
Declaration of Dr. Glenn Prestwich in Support of this IPR Petition, 99 Pages, Apr. 17, 2014.
Deland, "Intrathecal Toxicity Studies with Benzyl Alcohol", Toxicol Appl Pharmacol, 1973; 25(2):153.
Desai et al., J Pharm Sci Feb. 1995; 84 (2): 212-5.

Ekspert (in Polish), Expert Anti Aging, Sep./Oct. 2006, English Translation.
Eyre et al., Top Curr. Chem., 2005, vol. 247, pp. 207-229.
Falcone et al. "Crosslinked hyaluronic acid dermal fillers: a comparison of rheological properties." J Biomed Mater Res A. 87(1): 264-271 (2008).
Falcone et al. "Temporary polysaccharide dermal fillers: a model for persistence based on physical properties." Dermatol Surg. 35(8): 1238-1243 (2009).
Farley, Jon S., et al., "Diluting Lidocaine and Mepivacaine in Balanced Salt Solution Reduces the Pain of Intradermal Injection", Regional Anesthesia 19(1):48-51, 1994.
Frati, Elena, et al., "Degradation of hyaluronic acid by photosensitized riboflavin in vitro. Modulation of the effect by transition metals, radical quenchers, and metal chelators," Free Radical Biology Medicine 22 (7):1139-1144 (1997).
Fujinaga, Masahiko, et al., "Reproductive and Teratogenic Effects of Lidocaine in Sprague-Dawley Rats", Anesthesiology 65:626-632, 1986.
Gammaitoni, Arnold R., et al., "Pharmacokinetics and safety of continuously applied lidocaine patches 5%", Am J Health Syst Pharm, vol. 59, Nov. 15, 2002, pp. 2215-2220.
GinShiCel MH Hydroxy Propyl methyl Cellulose, Web Page http://www.ginshicel.en/MHPC.html, Nov. 12, 2008.
Gold MH, "Use of Hyaluronic acid fillers for the treatment of the aging face." Clin. Interventions Aging 2(3): 369-376 (2007).
Goldberg "Breakthroughs in US dermal fillers for facial soft-tissue augmentation." J Cosmet Laser Ther. 11(4): 240-247 (2009).
Graefe, Hendrik, et al., "Sensitive and specific photometric determination of mannitol in human serum," Clin Chem Lab Med. 41 (8):1049-1055 (2003).
Grecomoro et al., "Intra-Articular Treatment with Sodium Hyaluronate in Gonarthrosis" A Controlled Clinical Trial Versus Placebo, Pharmatherapeutica, 1987; 5(2):137-41.
Grillo et al., "Thermal Reconstitution of Collagen from Solution and the Response to Its Heterologous Implantation", JSR II, No. 1, pp. 69-82 (1962).
Hanke et al., "Effectiveness and durability of a hyaluronic acid 28 mg/ml, lidocaine 0.3% stable combination product as demonstrated in a multicenter, randomized trial", J. Am Acad Dermatol., 56(2) Supp 3, Feb. 2007. pAB94.
Hassan et al., Effects of Adjuvants to local anaesthetics on their duration. III. Experimental studies of hyaluronic acid. Abstract Pub Med [Acta Anesthesiol Scand. May 1985; 29(4):384-8].
Hayashibara, "AA2G"; Sep. 23, 2007, http://web.archive.org/web/2007923072010/http://www.hayashibara-intl.com/-cosmetics/aa2g.html.
Helary et al., "Concentrated collagen hydrogels as dermal substitutes", Biomaterials 31 (2010) 481-490.
Helliwell, "Use of an Objective Measure of Articular Stiffness to Record Changes in Finger Joints After Intra-Articular Injection of Corticosteroid", An Theum Dis, 1997; 56:7.
Hertzberger-Ten et al., "Intra-Articular Steroids in Pauciarticular Juvenile Chronic Arthritis", Type I, Eur J Ped 1991; 150:170-172.
Hetherington, "Potential for Patient Harm From Intrathecal Administration of Preserved Solutions", Med J Aust, 2000, 173(3):p. 141.
Hoffman, Klaud, "Volumizing effects of a smooth, highly cohesive, viscous 20-mg/mL hyaluronic acid volumizing filler: prospective European study", BMC Dermatology, 9:9 (2009).
Hurst, "Adhesive Arachnoiditis and Vascular Blockage Caused by Detergents and Other Chemical Irritants: an Experimental Study", J Path Bact, 1955; 70:167.
Intramed Mannitol 20% m/v Infusion, package insert, pp. 1-2 (2010) http://home.intekom.com/pharm/intramed/manit120.html.
Jones et al., "Intra-Articular Hyaluronic Acid Compared to Intra-Articular Triamcinolone Hexacetonide in Inflammatory Knee Osteoarthritis", Osteoarthritis Cartilage, 1995, 3:269-273.
Kablik et al. "Comparative physical properties of hyaluronic acid dermal fillers." Dermatol. Surg. Suppl. 35(Suppl. 1): 302-312 (2009).
Kinney, Brian M., "Injecting Puragen Plus Into the Nasolabial Folds: Preliminary Observations of FDA Trial", Aesthetic Surgery Journal, 26:741-748 (2006).

(56) References Cited

OTHER PUBLICATIONS

Klein, "Skin Filling Collagen and Other Injectables of the Skin", Dermatologic Clinics, Jul. 2001, vol. 19, No. 3, pp. 491-588, ix, XP00919589.
Kopp et al., The Short-Term Effect of Intra-Articular Injections of Sodium Hyaluronate and Corticosteroid on Temporomandibular Joint Pain and Dysfunction, J. Oral Maxillofacia Surgery, Jul. 1985, 43(6):429-35.
Kulicke et al., "Visco-Elastic Properties of Sodium Hyaluronate Solutions," American Institue of Physics (2008).
Laeschke, "Biocompatibility of Microparticles into Soft Tissue Fillers", 23 Semin. Cutan. Med. Surg., 214 (2004).
Lamar et al., "Antifibrosis Effect of Novel Gels in Anterior Ciliary Sclerotomy *ACS)," ARVO 2002 abstract.
Levy et al., "A Split-Face Comparison of Two Hyaluronic Acid Facial Fillers in the Treatment of Naso-labial Folds", Anti-Aging Medicine World Conference (AMWC), 6th Ed., Paris, France, Apr. 10-12, 2008, Final Program, p. 138.
Levy, et al., "A Split-Face Comparison of Two Hyaluronic Acid Facial Fillers in the Treatment of Naso-Labial Folds," Abstract of poster presented at the Anti-Aging Medicine World Congress (AMWC), 6th Edition, Paris, France, Apr. 10-12, 2008, in: Final Program of the 6th AMWC in Paris, Apr. 10-12, 2008, p. 138.
Levy, Jaime et al., "Lidocaine hypersensitivity after subconjunctival injection", Can J Ophthalmol 2006; 41:204-6.
Lindvall et al.; "Influence of Various Compunds on the Degradation of Hyaluronic Acid by a Myeloperoxidase System"; Chemico-Biological Interactions; vol. 90; pp. 1-12; 1994.
Lowry et al., "Thermal Stability of sodium hyaluronate in aqueous solution", Journal of Biomedical Materials Research, 28:1239-1244, 1994.
Lupo et al., "Effectiveness of next generation hyaluronic acid dermal fillers in the treatment of severe nasolabial folds", J.Am Acad Dermatol., 56(2) Supp 3, Feb. 2007, p. AB199.
Lupo, MP., "Hyaluronic acid fillers in facial rejuvenation." Semin. Cutan. Med. Surg. 25(3): 122-126 (2006).
Mackley, et al., "Delayed-Type Hypersensitivity to Lidocaine", Arch Dermatol, vol. 139, Mar. 2003, pp. 343-346.
Mancinelli et al., "Intramuscular High-Dose Triamcinolone Acetonide in the Treatment of Severe Chronic Asthma", West J. Med, Nov. 1997: 167(5), 322-329.
Matsumoto, Alan H, et al., "Reducing the Discomfort of Lidocaine Administration through pH Buffering," Journal of Vascular and Interventional Radiology, Jan.-Feb. 1994, pp. 171-175.
May 2, 2014—EP 2674147 Communication Pursuant to Rule 114(2) EPC Third Party Observations.
McCarty et al., "Inflammatory Reaction After Intrasynovial Injection of Microcrystalline Adrenocorticosteroid Esters", Arthritis and Rheumatism, 7(4):359-367 (1964).
McCleland, Plastric Reconstructive Surgery, 100(6), Nov. 1997, pp. 1466-1474.
McPherson, John M., "Development and Biochemical Characterization of Injectable Collagen," J. Dermatol Surg Oncol, 14 (Suppl1):Jul. 7, 1988, pp. 13-20.
Meeting of the General and Plastic Surgery Devices Panel, FDA Advisory Committee Briefing Document, Juvederm Voluma XC, PMA P110033, May 2, 2013.
Millay et al.; "Vasoconstrictors in Facial Plastic Surgery"; Archives of Otolaryngology-Head & Neck Surgery; vol. 117; pp. 160-163; Feb. 1991.
Monheit et al., "Juvederm: A Hyaluronic Acid Dermal Filler", J Drugs Dermatol. 6(11):1091-5, Nov. 2007.
Oct. 2, 2013—EP 2323617 Communication Pursuant to Rule 114(2) EPC Third Party Observations.
Orvisky, E., et al., "High-molecular-weight hyaluronan—A valuable tool in testing the antioxidative activity of amphiphilic drugs stobadine and vinpocetine," Pharm.Biomed.Anal. 16:419-424 (1997).
Osmitrol (generic name Mannitol),Official FDA Information, side effects and uses, pp. 1-10 (2010) http://www.drugs.com/pro/osmitrol.html.
Park et al., "Biological Characterization of EDC-crosslinked Collagen-Hyaluronic Acid Matrix in Dermal Tissue Restoration", Biomaterials 24 (2003) 1631-1641.
Park et al., "Characterization of Porous Collagen/Hyaluronic Acid Scaffold Modified by 1-ethyl-3-(3-dimethylaminopropyl)carbodiimide cross-linking", Biomaterials 23 (2002): 1205-1212.
Park et al., "In vireio evaluation of conjugated Hyalruonic acid with Ascorbic Acid", Journal of Bone & Joint Surgery, British vol. 92-B, XP-002706399, 2010.
Petition for Inter Partes Review, 74 Pages, Aug. 29, 2014.
Petition for Inter Partes Review, 76 Pages, Aug. 29, 2014.
Powell; "Stability of Lidocaine in Aqueous Solution: Effect of Temperature, pH, Buffer, and Metal Ions on Amide Hydrolysis"; Pharmaceutical Research; vol. 4, No. 1, 1987.
Prager et al., "A prospective split-face, randomized, comparative study of safety and 12-month longevity of three formulations of hyaluronic acid dermal filler for treatment of nasolabial folds", Dermatologic Surgery 38(7 Pt 2):1143-50, 2012.
Prestwich, Glenn D., "Evaluating drug efficacy and toxicology in three dimensions: using synthetic extracellular matrices in drug discovery," Accounts of Chemical Research 41 (1):139-148 (2008).
Product information about Juvederm Ultra Plus by Allergan, 24 Pages, 2010.
Rehakova, Milena, et al., "Properties of collagen and hyaluronic acid composite materials and their modifications by chemical crosslinking," Journal of Biomedical Research, vol. 30, 1996, pp. 36-372, XP002590342.
Remington's Pharmaceutical Science Mac Publishing Company, Easton, PA 16th Edition 1980.
Rosenblatt et al., "Chain Rigidity and Diffusional Release in Biopolymer Gels", Proceed. Inter. Symp. Control. Rel. Bioact. Mater., 20, pp. 264-265 (1993) Controlled Release Society, Inc.
Rosenblatt et al., "The Effect of Collagen Fiber Size Distribution on the Release Rate of Proteins from Collagen Matrices by Diffusion", J. Controlled Rel., 9, pp. 195-203 (1989).
Sannino et al., "Crosslinking of Cellulose Derivatives and Hyaluronic Acid with Water-Soluble Carbodiimide," Polymer 46 (2005)pp. 11206-11212.
Sculptra.RTM. Aesthetic (injectable poly-L-lactic acid) Directions for Use, Dermik Laboratories product insert (Jul. 2009), sanofi-aventis U.S. LLC.
Segura et al. "Crosslinked hyaluronic acid hydrogels: a strategy to functionalize and pattern." Biomaterials 26(4): 359-371 (2005).
Selvi et al, "Arthritis Induced by Corticosteroid Crystals", J. Rheumatology, 2004, 34:3.
Serban et al. "Modular Extracellular Matrices: Solutions for the Puzzle." Methods 45(1): 93-98 (2008).
Shu et al. "Synthesis and evaluation of injectable, in situ crosslinkable synthetic extracellular matrices for tissue engineering." J. Biomed. Mater. Res. A. 79(4): 902-912 (2006).
Silver et al., "Physical Properties of Hyaluronic Acid and Hydroxypropylmethylcellulose in Solution: Evaluation of Coating Ability," Journal of Applied Biomaterials, vol. 5, 89-98 (1994).
Skardal et al "Bioprinting Vessel-Like Constructs Using Hyaluronan Hydrogels Crosslinked with Tetrahedral Polyethylene Glyol Tetracrylates"; BioMaterials. Elsevier Science Publishers BV; vol. 31, No. 24; pp. 6173-6181; Aug. 1, 2010.
Smith, Kevin C., et al., "Five Percent Lidocaine Cream Applied Simultaneously to Skin and Mucosa of the Lips Creates Excellent Anesthesia for Filler Injections", Dermatol Surg 2005; 31:1635-1637.
Soltes et al., "Degradative Action of Reactive Oxygen Species on Hyaluronan", Biomacromolecules 7:659-668, 2006.
Stern et al., "The many ways to cleave hyaluronan", Biotechnology Advances 25 (2007) 537-557.
Summary of Safety and Effectiveness of Cosmetic Tissue Augmentation prduct (CTA), http://www.accessdata.fda.goc/scripts/cdrh/cfdocs/cftopic/pma/pma.-cfm?num=p050033, Issued Dec. 6, 2006, Updated Jan. 10, 2007, Accessed Jan. 2, 2014.
Tezel et al. "The science of hyaluronic acid dermal fillers." J. Cosmet. Laser Ther. 10(1): 35-42 (2008).
The European Aesthetic Guide, Spring 2008, pp. 120-122.

(56) References Cited

OTHER PUBLICATIONS

Toth et al., "Preclinical evaluation of a novel hyaluronic acid 28 mg/ml lidocaine 0.3% stable combination product", J. Am Acad Dermatol., 56(2) Supp 3, Feb. 2007, pAB94.
TRB Chemedica Opthalmic Line, Visiol, product info., pp. 1-2.
Visiol, Viscoelstic gel for use in ocular surgery, (2010) p. 1, htt://www.trbchemedica.com/index.php/option=com.sub.--content &tas.
Wahl, "European Evaluation of a New Hyaluronic Acid Filler Incorporating Lidocaine", Journal of Cosmetic Dermatology; vol. 7; pp. 298-303; 2008.
Waraszkiewicz, Sigmund M., et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, Nov. 1981, pp. 1215-1218.
Weidmann; "New Hyaluronic Acid Filler for Subdermal and Long-Lasting Volume Restoration of the Face"; European Dermatology; pp. 65-68; 2009.
Xia, Yun et al., "Comparison of Effects of Lidocaine Hydrochloride, Buffered Lidocaine, Diphenhydramine, and Normal Saline After Intradermal Injection", Journal of Clinical Anesthesia 14:339-343, 2002.
Yeom et al. "Effect of Cross-Linking Reagents for Hyaluronic Acid Hydrogel Dermal Fillers on Tissue Augmentation and Regeneration." Bioconjugate Chem., 21(2): 240-247 (2010).
Yui, Nobuhiko, et al., "Inflammation responsive degradation of crosslinked hyaluronic acid gels," Journal of Controlled release, 22 (1992) pp. 105-116.
Yui, Nobuhiko, et al., "Photo-responsive degradation of heterogeneous hydrogels comprising crosslinked hyaluronic acid and lipid microspheres for temporal drug delivery," Journal of Controlled Release, 26 (1993) pp. 141-145.
Yun, YH et al. "Hyaluronan Microspheres for Sustained Gene Delivery and Site-Specific Targeting", Biomaterials, vol. 25, 2004, pp. 147-157.
Zheng et al. "In situ crosslinkable hyaluronan hydrogels for tissue engineering." Biomaterials 25(7-8): 1339-1348 (2004).
Zulian et al., Triamcinolone Acetonide and Hexacetonide Intra-Articular Treatment of Symmetrical Joints in Juvenile Idiopathic Arthritis: a Double-Blind Trial, Rheum 2004.
"Experimental Data" provided by Opponent, 2016, 7 pages.
U.S. Appl. No. 12/393,768 Final OA, dated Nov. 19, 2012, 10 pages.
U.S. Appl. No. 12/393,768 Non-final OA dated Feb. 3, 2012, 10 pages.
U.S. Appl. No. 12/393,768 Non-final OA dated May 31, 2011, 15 pages.
U.S. Appl. No. 12/393,884 Final OA, dated Dec. 27, 2011, 11 pages.
U.S. Appl. No. 12/393,884 Non-final OA, dated May 31, 2011, 10 pages.
Carruthers et al. "Volumizing with a 20-mg/ml Smooth, Highly Cohesive, Viscous Hyaluronic Acid Filler and its Role in Facial Rejuvenation Therapy," Dermatologic Surgery, Nov. 2010, pp. 1886-1892.
Clark III, "Animal-Based Hyaluronic Acid Fillers: Scientific and Technical Considerations," Plastic and Reconstructive Surgery, Nov. 2007, Supplement 27s, 6 pages.
Cordoro, "Topical Therapy for the Management of Childhood Psoriasis: Part 1," Skin Therapy Letter, Apr. 2008, vol. 13, No. 3, 8 pages.
Dale P. De Vore, CV, Aug. 2017, 22 pages.
Elevess product information by Anika Therapeutics, Jul. 2008, 6 pages.
EP 04742458.5 Boards of Appeal of the European Patent Office, May 11, 2012, Decision (in French) 14 pages.
EP 2323617 Communication of Notices of Opposition, Allergan Industrie SAS, 147 001 a/jme, Nov. 23, 2017, 2 pages.
EP 2323617 Communication Pursuant to Rule 114(2) EPC Third Party Observations, Dec. 19, 2013, 22 pages.

EP 2323617 Communication Pursuant to Rule 114(2) EPC Third Party Observations, Jan. 2, 2017, 3 pages.
EP 2323617 Communication Pursuant to Rule 114(2) EPC Third Party Observations, Nov. 18, 2015, 8 pages.
EP 2323617 Communication Pursuant to Rule 114(2) EPC Third Party Observations, Nov. 8, 2016, 4 pages.
EP 2323617 Notice of Opposition, dated Oct. 13, 2017, 38 pages.
EP 2323617 Notice of Opposition, dated Oct. 17, 2017, 55 pages.
EP 2323617 Notice of Opposition, dated Oct. 18, 2017, 18 pages.
EP 2323617 Notice of Opposition, dated Oct. 2, 2017, 18 pages.
EP 2323617 Notice of Opposition, dated Sep. 27, 2017, 56 pages.
EP 2323617 Notice of Opposition, dated Sep. 29, 2017, 56 pages.
EP 2326302, Commencement of Proceedings Before the Board of Appeal, Jan. 2, 2019, 4 pages.
EP 2326302, Decision Revoking the EP Patent, Dec. 3, 2018, 5 pages.
EP 2637710 Communication of Notices of Opposition, Allergan Industrie SAS, Jan. 23, 2018, 2 pages.
EP 2637710 Communication Pursuant to Rule 114(2) EPC Third Party Observations, Aug. 26, 2015, 121 pages.
EP 2637710 Communication Pursuant to Rule 114(2) EPC Third Party Observations, Feb. 1, 2016, 13 pages.
EP 2637710 Communication Pursuant to Rule 114(2) EPC Third Party Observations, Nov. 8, 2016, 4 pages.
EP 2637710 Notice of Opposition, dated Dec. 19, 2017, 48 pages.
EP 2637710 Notice of Opposition, dated Jan. 4, 2018, 12 pages.
EP 2637710 Notice of Opposition, dated Jan. 4, 2018, 31 pages.
EP 2637710 Notice of Opposition, dated Jan. 4, 2018, 5 pages.
EP 2637710 Notice of Opposition, dated Jan. 4, 2018, 6 pages.
EP 2674147, Communication Pursuant to Rule 114(2) EPC Third Party Observations, Apr. 5, 2018, 81 pages.
EP 2674147, Communication Pursuant to Rule 114(2) EPC Third Party Observations, dated Dec. 14, 2018, 19 pages.
EP 2674147, Communication Pursuant to Rule 114(2) EPC Third Party Observations, May 2, 2014, 32 pages.
EP 2674147, Communication Pursuant to Rule 114(2) EPC Third Party Observations, Nov. 14, 2016, 3 pages.
EP 2674147, Communication Pursuant to Rule 114(2) EPC Third Party Observations, Nov. 8, 2018, 4 pages.
EP 2674147, Communication Pursuant to Rule 114(2) EPC Third Party Observations, Nov. 9, 2018, 9 pages.
EP 3138586, Third Party Observations, Oct. 30, 2018, 5 pages.
EP 3205332 Communication Pursuant to Rule 114(2) EPC Third Party Observations, Oct. 26, 2018, 10 pages.
Eppley et al., "Injectable Soft-Tissue Fillers: Clinical Overview," Plastic and Reconstructive Surgery, Sep. 2006, pp. 98e-106e.
Fagien et al., A Brief Overview and History of Temporary Fillers: Evolution, Advantages, and Limitations, Plastic and Reconstructive Surgery, Nov. 2007, Supplement 8S, 8 pages.
Federal Register, Notices, Apr. 3, 2007, vol. 72, No. 63, pp. 15886-15887.
Harding et al. "Molecular Weight Determination of Polysaccharides," Advances in Carbohydrate Analysis, 1991, vol. 1, pp. 63-144.
Internet Printout Showing Earlier Publication Date of Carruthers et al. "Volumizing with a 20-mg/ml Smooth, Highly Cohesive, Viscous Hyaluronic Acid Filler and its Role in Facial Rejuvenation Therapy," Published online Oct. 22, 2010, 2 pages.
Juvederm Ultra 3 package insert, Sep. 25, 2012, 4 pages.
Juvederm Ultra and Ultra Smile Information, retrieved from https://www.consultingroom.com/treatment/juvederm-ultra, Oct. 2017, 6 pages.
Mahmoud et al., "An Update on New and Emerging Options for the Treatment of Vitiligo," Skin Therapy Letter, Mar. 2008, vol. 13, No. 2, 10 pages.
Matarasso, "Understanding and Using Hyaluronic Acid," Aesthetic Surgery Surgery Journal, Jul./Aug. 2004, pp. 361-364.
McCracken et al., "Hyaluronic Acid Gel (Restylane) Filler for Facial Rhytids: Lessons Learned from American Society of Ophthalmic Plastic and Reconstructive Surgery Member Treatment of 286 Patients," Ophthalmic Plastic and Reconstructive Surgery, 2006, vol. 22, No. 3, pp. 188-191.

(56) References Cited

OTHER PUBLICATIONS

Mezger, "The Rheology Handbook: For Users of Rotational Oscillatory Rheometers," Vincentz Network GmbH, 2006, pp. 208-209.
Molecular Weight: The Number Average Molecular Weight, 2005, The University of Southern Mississippi, Polymer Science Learning Center, 5 pages.
Narins et al., "Injectable Skin Fillers," Clin Plastic Surg, 2005, vol. 32, pp. 151-162.
Newburger, "Cosmetic Medical Devices and Their FDA Regulation," Arch Dermatol, Feb. 2006, vol. 142, pp. 225-228.
Package insert of Juvederm Ultra 3, 2007, 2 pages.
U.S. Appl. No. 61/087,934, filed Aug. 11, 2008.
U.S. Appl. No. 61/096,278, filed Sep. 11, 2008.
U.S. Appl. No. 61/085,956, filed Aug. 4, 2008, 55 pages.
Rohrich et al., "The Role of Hyaluronic Acid Fillers (Restylane) in Facial Cosmetic Surgery: Review and Technical Considerations," Plastic and Reconstructive Surgery, Nov. 2007, Supplement 41S, 14 pages.
Sapijaszko, "Dermal Fillers: Ever-Expanding Options for Esthetic Use," Skin Therapy Letter, Oct. 2007, vol. 12, No. 8, 4 pages.
Smith, "Practical Use of Juvederm: Early Experience," Plastic and Reconstructive Surgery, Nov. 2007, Supplement 67S, 7 pages.
Tableau comparatif demandes prioritaires du brevet oppose, 2 pages, submitted by opponent, 2017.
Tan, "New Developments in Hormonal Therapy for Acne," Skin Therapy Letter, Sep. 2007, vol. 12, No. 7, 8 pages.
Tezel et al. "Comparison of extrusion forces of different hyaluronic acid dermal fillers," American Academy of Dermatology 65th Annual Meeting, Feb. 2007, 1 page.
Wahl, "The Juvederm Ultra 3 European Expert Evaluation," 2008, 1 page.
Wahl, "The Juvederm Ultra European Expert Evaluation," Abstract of poster, 2008 Anti-Aging Medicine World Congress, 1 page.
Wikipedia-Auszug "Mark-Houwink-Gleichung", retrieved from https://de.wikipedia.org/wiki/Mark-Houwink-Gleichung on Dec. 7, 2017, 3 pages, including English language translation.
Wikipedia-Auszug "Molmassenverteilung", retrieved from https://de.wikipedia.org/wiki/molmassenverteilung on Dec. 7, 2017, 9 pages including English language translation.
Allergan Patent Notices, Available at https://www.allergan.com/products/patents, downloaded on Apr. 15, 2014.
Illustration of the Hylacross technology used to prepare Juvederm (without lidocaine) and Juvederm XC (with lidocaine), available at http://www.juvederm.com/content/pdf/juvedermsmooth.pdf, 2010.
Judeverm Ultra label, product information about Juvederm Ultra by Allergan, available as of Aug. 24, 2017.
Judeverm Ultra Plus label, product information about Juvederm Ultra Plus by Allergan, available as of Aug. 24, 2017.
Juveverm Ultra Plus XC label, product information about Juvederm Ultra Plus XC by Allergan, Aug. 16, 2010.
Judeverm Ultra XC label, product information about Juvederm Ultra XC by Allergan, Aug. 16, 2010.
Judeverm Voluma label, product information about Juvederm Voluma by Allergan, available as of Aug. 24, 2017.
Judeverm Voluma XC label, product information about Juvederm Voluma XC by Allergan, Nov. 26, 2010.
Dermal Fillers Approved by the Center for Devices and Radiological Health, available at https://fda.gov/MedicalDevices/ProductsandMedicalProcedures/CosmeticDevices/WrinkleFillers/ucm227749.htm#approved, 3 pages downloaded on Aug. 2, 2017.
Medicis, Perlane®, 2006, pp. 1-23.
EP 2323617 Translated Brief of Opponent Farco dated Feb. 15, 2019, 36 pages.
ROMPP Lexikon der Chemie, 10th ed, 1997, p. 2405, key word: "Lidocaine", with English language translation.
U.S. Appl. No. 15/443,080, filed Feb. 27, 2017.
U.S. Appl. No. 14/754,504, filed Jun. 29, 2015.
U.S. Appl. No. 14/242,752, filed Apr. 1, 2014.
U.S. Appl. No. 13/419,079, filed Mar. 13, 2012.
U.S. Appl. No. 12/393,884, filed Feb. 26, 2009.

Defendants' Answer and Counterclaims to Plaintiff's Complaint, *Allergan USA, Inc. and Allergan Industrie SAS v. Prollenium US Inc. and Prollenium Medical Technologies Inc.*, C.A. No. 19-126-CFC, filed May 6, 2019, 33 pages.
Claim Construction Order, *Allergan USA v. Medicis Aesthetics, Inc.*, No. 8:13-cv-01436-AG-JPR, slip op. Aug. 12, 2014, ECF No. 79, also available at 2014 WL 5488895, 21 pages.
CTA Product Insert, 2006, 12 pages.
Declaration of Dale Devore, Ph.D., dated Aug. 23, 2019, 100 pages.
FDA Letter to Anika Therapeutics, Inc. dated Dec. 20, 2007, 7 pages.
Lebreton Declaration dated May 2, 2012, 3 pages.
Monheit, Hyaluronic Acid Fillers: Hylaform and Captique, Facial Plastic Surgery Clinics, vol. 15, No. 1, 77-87, Feb. 2007.
Öhrlund et al., "Extrusion Force and Syringe Dimensions of Two Hyaluronic Acid Dermal Fillers," 8th Anti-aging Medicine World Congress (AMWC), Apr. 2010, 1 page.
Peition for IPR of U.S. Pat. No. 8,450,475 by Galderma S.A. and Q-Med AB, IPR No. 2014-01417, Paper 4, filed Aug. 29, 2019, 66 pages.
Petition for IPR of U.S. Pat. No. 8,450,475 by Teoxane S.A., IPR No. 2017-02002, Paper 1, filed Aug. 29, 2017, 68 pages.
Petition for IPR of U.S. Pat. No. 8,357,795 by Galderma S.A. and Q-Med AB, IPR No. 2014-01422, Paper 4, filed Aug. 29, 2014, 67 pages.
Petition for IPR of U.S. Pat. No. 8,357,795 by Teoxane S.A., IPR No. 2017-01906, Paper 1, filed Aug. 2, 2017, 66 pages.
Pinsky et al., "Juvederm Injectable Gel: A Multicenter, Double-Blind, Randomized Study for Safety and Effectiveness," Aesthetic Surgery Journal, vol. 28, Issue 1, Jan./Feb. 17-23 2008).
Premarket Approval (PMA) Supplement Summary Review Memo for P050047/S005, Han. 6, 2010 available at https://www.accessdata.fda.gov/scripts/cdrh/cfdocs/cfmpa/pma.cfm?id=P050047S005, 6 pages.
Prevelle Silk; PMA P030032, dated Jun. 6, 2017, 2 pages.
Sarnoff et al., "Comparison of Filling Agents for Lip Augmentation," Aesthetic Surgery Journal, vol. 28, Issue 5, 556-563, Sep./Oct. 2008.
Transcript of Claim Construction Hearing, *Allergan USA, Inc v. Medicis Aesthetics, Inc.*, No. 8:13-cv-01436-AG-JPR (Aug. 12, 2014), ECF No. 81, 41 pages.
U.S. Appl. No. 12/393,768, Applicant Initiated Interview Summary dated Feb. 6, 2013, 5 pages.
U.S. Appl. No. 12/393,768, Notice of Allowance dated Mar. 25, 2013, 10 pages.
U.S. Appl. No. 12/393,768, Response to Office Action dated Jul. 30, 2012, 14 pages.
U.S. Appl. No. 12/393,768 Response to Office Action dated Nov. 9, 2011, 12 pages.
U.S. Appl. No. 12/393,884, Claims dated Feb. 26, 2009, 5 pages.
U.S. Appl. No. 12/393,884, Notice of Allowance dated Aug. 6, 2012, 10 pages.
U.S. Appl. No. 12/393,884, Response to Final Office Action dated Jun. 14, 2012, 27 pages.
U.S. Appl. No. 12/393,884, Response to Office Action dated Sep. 29, 2011, 16 pages.
U.S. Appl. No. 13/419,079, Notice of Allowance dated Jul. 18, 2014, 10 pages.
U.S. Appl. No. 13/746,170, Notice of Allowance dated Sep. 9, 2015, 69 pages.
U.S. Appl. No. 13/746,170, Response dated May 4, 2015, 4 pages.
U.S. Appl. No. 13/891,052, Notice of Allowance dated Feb. 5, 2016, 19 pages.
U.S. Appl. No. 14/242,747, Notice of Allowance dated Apr. 14, 2015, 10 pages.
Update on Drugs, Skin Therapy Letter, vol. 12, No. 7, p. 8, Sep. 2007.
Update on Drugs, Skin Therapy Letter, vol. 13, no. 3, p. 8, Apr. 2008.
Update on Drugs, Skin Therapy Letter, vol. 15, No. 3, p. 6, Mar. 2010.
EP2323617—Written submission in preparation to/during oral proceedings, opposition by Nestle Skin Health SA, Sep. 12, 2019, 8 pages.

(56) References Cited

OTHER PUBLICATIONS

EP2323617—Written submission in preparation to/during oral proceedings, opposition by Merz Pharma GmbH, Sep. 12, 2019, 16 pages.
EP2323617—Written submission in preparation to/during oral proceedings, opposition by Laboratories Vivacy, Sep. 12, 2019, 16 pages.
*Allergan USA Inc and Allergan Industrie SAS v. Prollenium US Inc and Prollenium Medical Technologies Inc.*, C.A. No. 19-126 (CFC), "Defendants Prollenium US Inc. and Prollenium Medical Technologies Inc.'s Invalidity Contentions," Sep. 30, 2019, 139 pages.
Weinkle et al., "A multi-center, double-blind, randomized controlled study of the safety and effectiveness of Juvederm injectable gel with and without lidocaine," J. Cosmet Dermatol., Sep. 2009, vol. 8, No. 3, 9 pages.
Mentor Corp Announces FDA Approval of Prevelle Silk, www.businesswire.com "Prevelle Silk Approval," Mar. 21, 2008, 2 pages.
Petition for IPR of U.S. Pat. No. 8,450,475 by Prollenium US Inc., IPR No. 2019-01505, filed Sep. 3, 2019, 83 pages.
Petition for IPR of U.S. Pat. No. 9,238,013 by Prollenium US Inc., IPR No. 2019-01508, filed Aug. 23, 2019, 74 pages.
Petition for IPR of U.S. Pat. No. 9,358,322 by Prollenium US Inc., IPR No. 2019-1509, filed Sep. 3, 2019, 81 pages.
Petition for IPR of U.S. Pat. No. 8,822,676 by Prollenium US Inc., IPR No. 2019-01617, filed Sep. 16, 2019, 80 pages.
Petition for IPR of U.S. Pat. No. 8,357,795 by Prollenium US Inc., IPR No. 2019-01632, filed Sep. 20, 2019, 74 pages.
Petition for IPR of U.S. Pat. No. 8,357,795 by Prollenium US Inc., IPR No. 2019-01506, filed Sep. 20, 2019, 84 pages.

\* cited by examiner

HYALURONIC ACID-BASED GELS INCLUDING LIDOCAINE

CROSS REFERENCE TO RELATED APPLICATIONS

This application is a continuation of U.S. patent application Ser. No. 15/443,080, filed on Feb. 27, 2017, which is a continuation of U.S. patent application Ser. No. 14/754,504, filed on Jun. 29, 2015, which is a continuation of U.S. patent application Ser. No. 14/242,752, filed on Apr. 1, 2014, which is a continuation of U.S. patent application Ser. No. 13/419,079, filed Mar. 13, 2012, now U.S. Pat. No. 8,822,676, which is a continuation of U.S. patent application Ser. No. 12/393,884, filed Feb. 26, 2009, now U.S. Pat. No. 8,357,795, which claims the benefit of each of U.S. Provisional Patent Application No. 61/085,956, filed Aug. 4, 2008, U.S. Provisional Patent Application No. 61/087,934, filed Aug. 11, 2008, and U.S. Provisional Patent Application No. 61/096,278, filed Sep. 11, 2008, the entire disclosure of each of these applications being incorporated herein by this reference.

FIELD OF THE INVENTION

The present invention generally relates to injectable soft tissue fillers and more specifically relates to hyaluronic acid-based dermal and subdermal fillers including an anesthetic agent.

BACKGROUND

It is generally accepted that as a person ages, the face begins to show effects of gravity, sun-exposure, and years of facial muscle movement, such as smiling, frowning, chewing and squinting. The underlying tissues that keep the skin appearing youthful begin to break down, often resulting in laugh lines, smile lines, "crow's feet" and facial creases often referred to as the "effects of aging."

In an effort to treat or correct the effects of aging, soft tissue fillers have been developed to help fill in facial lines and depressions and for restoring fat loss-related tissue volume loss. The soft tissue fillers thereby temporarily restore a smoother, more youthful appearance.

Ideally, soft tissue fillers are long-lasting, soft, smooth and natural appearing when implanted in the skin or beneath the skin. Further, soft tissue fillers are easy to implant into a patient using a fine gauge needle and require low extrusion force for injection. Ideal fillers would also cause no adverse side effects, and would be injectable with minimal or no discomfort to the patient.

Collagen based soft tissue fillers were developed over 20 years ago, and for some time, bovine collagen-based fillers were the only U.S. Food and Drug Administration (FDA)-approved dermal fillers. Because these dermal fillers are bovine based, one of the main disadvantages has been the potential for allergic reaction in patients. It is believed that approximately 3-5% of human subjects show serious allergic reactions to bovine collagen, thus requiring careful testing before using these fillers in any particular person. In addition to allergic reactions, collagen based fillers degrade rapidly upon injection and require frequent treatments to sustain a smoother, more youthful appearance.

In February 2003, human-derived collagen filler compositions received FDA approval. These collagens provide the advantage of a significantly reduced risk of allergic reactions. However, despite the reduced incidence of allergic reactions, the human derived collagen fillers still suffered from the rapid degradation of the injected product.

The search for fillers that do not provoke allergic reactions and sustain a smoother, more youthful appearance has brought about the development of hyaluronic acid (HA)-based products. In December 2003, the first HA-based filler was approved by the FDA. This was rapidly followed by the development of other HA-based fillers.

HA, also known as hyaluronan, is a naturally occurring, water soluble polysaccharide, specifically a glycosaminoglycan, which is a major component of the extra-cellular matrix and is widely distributed in animal tissues. HA has excellent biocompatibility and does not cause allergic reactions when implanted into a patient. In addition, HA has the ability to bind to large amounts of water, making it an excellent volumizer of soft tissues.

The development of HA-based fillers which exhibit ideal in vivo properties as well as ideal surgical usability has proven difficult. For example, HA-based fillers that exhibit desirable stability properties in vivo, can be so highly viscous that injection through fine gauge needles is difficult. Conversely, HA-based fillers that are relatively easily injected through fine gauge needles often have relatively inferior stability properties in vivo.

One method to overcome this problem is to use crosslinked HA-based fillers. Crosslinked HA is formed by reacting free HA with a crosslinking agent under suitable reaction conditions. Methods of preparing HA based soft tissue fillers including both crosslinked and free HA are well known.

It has been proposed to incorporate certain therapeutic agents, for example, anesthetic agents such as lidocaine, into injectable HA-based compositions. Unfortunately, HA-based injectable compositions which incorporate lidocaine during the manufacturing process are prone to partial or almost complete degradation prior to injection, particularly during high temperature sterilization steps and/or when placed in storage for any significant length of time.

It is an objective of the HA-based soft filler compositions and methods of making and using them as described herein to provide soft tissue fillers that do not cause allergic reactions in patients, are biocompatible and are stable and usable in vivo and include one or more local anesthetic agents.

SUMMARY

The present description relates to soft tissue fillers, for example, dermal and subdermal fillers, based on hyaluronic acid (HA) and pharmaceutically acceptable salts of HA, for example, sodium hyaluronate (NaHA). HA-based compositions described herein include a therapeutically effective amount of at least one anesthetic agent. In one embodiment, for example, the anesthetic agent is lidocaine. The present HA-based compositions including at least one anesthetic agent have an enhanced stability, relative to conventional HA-based compositions including, for example, lidocaine, when subjected to sterilization techniques such as autoclaving, and/or when stored for long periods at ambient temperature. Methods for preparing such HA-based compositions are also provided as well as products made by such methods.

Described herein are soft tissue filler compositions, the compositions generally comprising: a hyaluronic acid component crosslinked with a crosslinking agent selected from the group consisting of 1,4-butanediol diglycidyl ether (BDDE), 1,4-bis(2,3-epoxypropoxy)butane, 1,4-bisglycidyloxybutane, 1,2-bis(2,3-epoxypropoxy)ethylene and 1-(2,3- epoxypropyl)-2,3-epoxycyclohexane, and 1,4-butanediol diglycidyl ether; and at least one anesthetic agent combined with the crosslinked HA component.

In yet another embodiment, the at least one anesthetic agent is lidocaine. In a further embodiment, the amount of the anesthetic agent is present at a concentration between about 0.1% and about 5.0% by weight of the composition. In still another embodiment, the anesthetic agent is present at a concentration between about 0.2% and about 1.0% by weight of the composition. In one embodiment, the anesthetic agent is lidocaine and is present at a concentration of about 0.3% by weight of the composition.

In still another embodiment, the soft tissue filler composition has an extrusion force of between about 10 N and about 13 N, for example, at a rate of about 12.5 mm/minute. In yet another embodiment, the composition has a viscosity of between about 5 Pa*s and about 450 Pa*s, for example, when measured at about 5 Hz.

In one embodiment, the HA component is a gel, for example, a cohesive, hydrated gel. In one embodiment, the HA component is a crosslinked HA gel having no greater than about 1% to about 10% free HA. For purposes of this disclosure, free HA includes truly free HA as well as lightly crosslinked HA chains and fragments, all in soluble form in water.

In yet other embodiments, the HA component comprises greater than about 10%, for example, greater than about 15%, for example, up to or greater than about 20% free HA.

In yet another embodiment, the HA component is a gel comprising particles of crosslinked HA in a relatively fluidic medium of free HA. In some embodiments, the HA component has an average particle size of greater than about 200 µm, for example, greater than about 250 µm.

Further described herein is a soft tissue filler composition comprising: a HA component crosslinked with 1,4-butanediol diglycidyl ether (BDDE), said HA component having a degree of crosslinking of less than about 5%, for example, about 2%, and an anesthetic component having a concentration between about 0.1% and about 5.0% by weight of the soft tissue filler composition, wherein the anesthetic is lidocaine.

Further described herein are methods of preparing soft tissue filler compositions, the methods comprising the steps of: providing a HA component crosslinked with at least one crosslinking agent selected from the group consisting of 1,4-butanediol diglycidyl ether (BDDE), 1,4-bis(2,3-epoxypropoxy)butane, 1,4-bisglycidyloxybutane, 1,2-bis(2,3-epoxypropoxy)ethylene and 1-(2,3-epoxypropyl)-2,3-epoxycyclohexane, and 1,4-butanediol diglycidyl ether or combinations thereof; adjusting the pH of said HA component to an adjusted pH above about 7.2; and adding a solution containing at least one anesthetic agent to the HA component having the adjusted pH to obtain a HA-based filler composition.

In another embodiment, the composition is sterilized, for example, by autoclaving, to form a sterilized composition and wherein the sterilized composition is stable at ambient temperature for at least about months, for example, at least 9 months, at least about 12 months, for example, at least about 36 months, or more.

In still another embodiment, the adjusted pH is above about 7.5. In another embodiment, the method further comprises the step of homogenizing the HA component during or after the step of adding the solution containing the at least one anesthetic agent. In a further embodiment, the step of homogenizing comprises subjecting the composition to mixing with a controlled shear.

In another embodiment, the step of providing a HA component comprises providing dry free NaHA material and hydrating the dry free NaHA material in an alkaline solution to obtain an alkaline, free NaHA gel. In yet another embodiment, the alkaline, free NaHA gel has a pH greater than about 8.0. In still another embodiment the pH is greater than about 10.

In a further embodiment, the HA component comprises greater than about 20% free HA and the crosslinked portion of the HA component has a degree of crosslinking of less than about 6% or less than about 5%.

In still a further embodiment, the soft tissue filler composition has a particulate nature in that it comprises particles of crosslinked HA dispersed in a fluid soluble HA medium. In some embodiments, the average size of such particles is at least about 200 µm, and in other embodiments the average size of such particles is at least about 250 µm.

Further described herein is a soft tissue filler composition comprising: a hyaluronic acid (HA) component crosslinked with 1,4-butanediol diglycidyl ether (BDDE), said HA component having a degree of crosslinking of less than about 5%, and an anesthetic component having a concentration between about 0.1% and about 5.0% by weight of the soft tissue filler composition, wherein the anesthetic is lidocaine.

In a specific embodiment of the invention, a method of preparing a soft tissue filler composition is further described, the method comprising the steps of: providing dry free NaHA material and hydrating the dry free NaHA material in an alkaline solution to obtain an alkaline, free NaHA gel; crosslinking the free NaHA gel with BDDE to form a crosslinked alkaline HA composition with a degree of crosslinking less than about 5% and a pH above about 7.2; adding a solution containing lidocaine HCl to the HA component having the adjusted pH to obtain said HA-based filler composition; homogenizing the HA-based filler composition thereby forming a homogenized HA-based filler composition; and sterilizing the homogenized HA-based filler composition thereby forming a sterilized HA-based filler composition, wherein the soft tissue filler composition has a particle size of greater than about 200 µm, for example, a particle size of greater than about 250 µm.

DEFINITIONS

Figure 1:
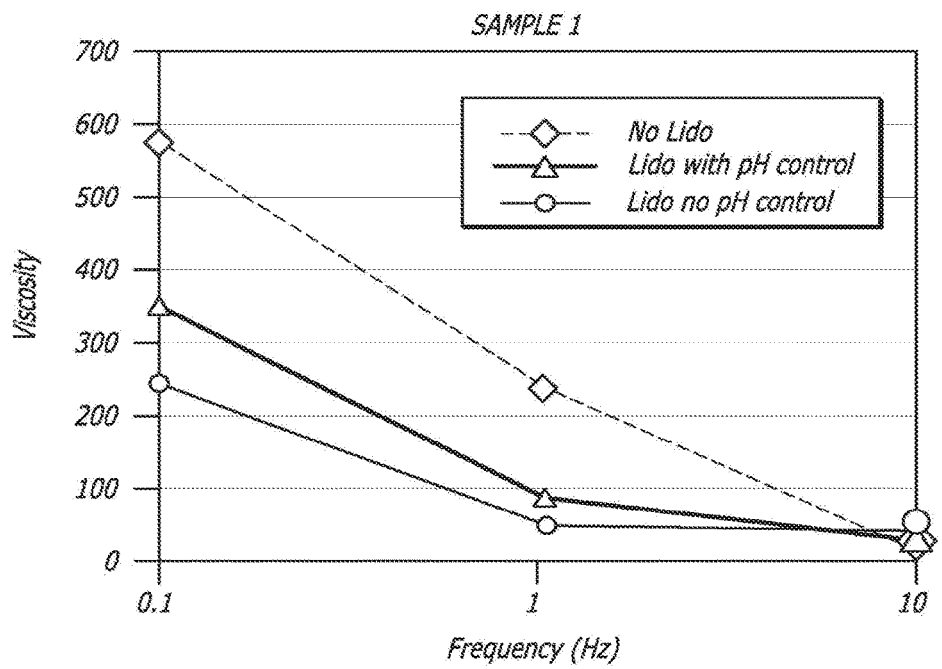
FIG. 1 graphically illustrates the viscosity of Sample 1 prepared without lidocaine, with lidocaine and pH adjustment during formation and with lidocaine but without pH adjustment during formation versus the shear frequency.

Certain terms as used in the specification are intended to refer to the following definitions, as detailed below. Where the definition of terms departs from the commonly used meaning of the term, applicant intends to utilize the definitions provided below, unless specifically indicated.

Autoclave stable or stable to autoclaving as used herein describes a product or composition that is resistant to degradation such that the product or composition maintains at least one, and preferably all, of the following aspects after effective autoclave sterilization: transparent appearance, pH, extrusion force and/or rheological characteristics, hyaluronic acid (HA) concentration, sterility, osmolarity, and lidocaine concentration.

Centrifugation as used herein refers to the process of using centrifugal forces to evenly distribute substances of greater and lesser density. Centrifugation is commonly used to separate a liquid phase from a solid or gel phase. Substantial phase separations resulting from centrifugation would be at least those visible by the naked eye, for example, a liquid phase and a solid phase distinctly separated when viewed with the naked eye.

High molecular weight HA as used herein describes a HA material having a molecular weight of at least about 1.0 million Daltons (mw$\geq 10^6$ Da or 1 MDa) to about 4.0 MDa. For example, the high molecular weight HA in the present compositions may have a molecular weight of about 2.0 MDa. In another example, the high molecular weight HA may have a molecular weight of about 2.8 MDa.

Low molecular weight HA as used herein describes a HA material having a molecular weight of less than about 1.0 MDa. Low molecular weight HA can have a molecular weight of between about 200,000 Da (0.2 MDa) to less than about 1.0 MDa, for example, between about 300,000 Da (0.3 MDa) to about 750,000 Da. (0.75 MDa).

Degree of Crosslinking as used herein refers to the intermolecular junctions joining the individual HA polymer molecules, or monomer chains, into a permanent structure, or as disclosed herein the soft tissue filler composition. Moreover, degree of crosslinking for purposes of the present disclosure is further defined as the percent weight ratio of the crosslinking agent to HA-monomeric units within the crosslinked portion of the HA based composition. It is measured by the weight ratio of HA monomers to crosslinker (HA monomers:crosslinker).

Free HA as used herein refers to individual HA polymer molecules that are not crosslinked to, or very lightly crosslinked to (very low degree of crosslinking) the highly crosslinked (higher degree of crosslinking) macromolecular structure making up the soft tissue filler composition. Free HA generally remains water soluble. Free HA can alternatively be defined as the "uncrosslinked," or lightly crosslinked component of the macromolecular structure making up the soft tissue filler composition disclosed herein.

Cohesive as used herein is the ability of a HA-based composition to retain its shape and resist deformation. Cohesiveness is affected by, among other factors, the molecular weight ratio of the initial free HA, the degree of crosslinking, the amount of residual free HA following crosslinking, and HA-based composition pH. Moreover, a cohesive HA-based composition resists phase separation when tested according to the method disclosed at Example 1 herein.

DETAILED DESCRIPTION

The present disclosure generally relates to soft tissue fillers, for example, dermal and subdermal fillers, based on hyaluronic acids (HA) and pharmaceutically acceptable salts of HA, for example, sodium hyaluronate (NaHA). In one aspect, HA-based compositions described herein include a therapeutically effective amount of at least one anesthetic agent, for example, lidocaine. The present HA-based compositions including at least one anesthetic agent have an enhanced stability, relative to conventional HA-based compositions including, for example, lidocaine, when subjected to high temperatures and pressures, for example, those experienced during heat and/or pressure sterilization techniques, for example, autoclaving, and/or for example, when stored at ambient temperature for an extended period of time.

The stable compositions maintain at least one of, or all of, the following aspects after effective autoclave sterilization and/or prolonged storage: transparent appearance, pH for use in a patient, extrusion force and/or rheological characteristics, HA concentration, sterility, osmolarity, and lidocaine concentration. Methods or processes of preparing such HA-based compositions are also provided as well as products made by such methods or processes.

As used herein, hyaluronic acid (HA) can refer to any of its hyaluronate salts, and includes, but is not limited to, sodium hyaluronate (NaHA), potassium hyaluronate, magnesium hyaluronate, calcium hyaluronate, and combinations thereof.

Generally, the concentration of HA in the compositions described herein is preferably at least 10 mg/mL and up to about 40 mg/mL. For example, the concentration of HA in some of the compositions is in a range between about 20 mg/mL and about 30 mg/mL. Further, for example, in some embodiments, the compositions have a HA concentration of about 22 mg/mL, about 24 mg/mL, about 26 mg/mL, or about 28 mg/mL.

In addition, the concentration of one or more anesthetics is in an amount effective to mitigate pain experienced upon injection of the composition. The at least one local anesthetic can be selected from the group of ambucaine, amolanone, amylocaine, benoxinate, benzocaine, betoxycaine, biphetamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, fomocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octocaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof. In one embodiment, the at least one anesthetic agent is lidocaine, such as in the form of lidocaine HCl. The compositions described herein may have a lidocaine concentration of between about 0.1% and about 5% by weight of the composition, for example, about 0.2% to about 1.0% by weight of the composition. In one embodiment, the composition has a lidocaine concentration of about 0.3% of the composition. The concentration of lidocaine in the compositions described herein can be therapeutically effective meaning the concentration is adequate to provide a therapeutic benefit without inflicting harm to the patient.

In one aspect of the invention, a method is provided for preparing a HA-based composition including an effective amount of lidocaine wherein the method comprises providing a precursor composition comprising a cohesive crosslinked HA-based gel, adding a solution containing lidocaine, for example in the form of lidocaine HCl, thereto and homogenizing the mixture to obtain a cohesive, at least partially crosslinked, HA-based composition including lidocaine that is stable to autoclaving. The cohesive, crosslinked HA-based gel includes no greater than about 1% to about 10% of free HA material by volume, for example, no greater than about 5% free HA material.

In some embodiments of the present invention, the HA component of the present compositions, hereinafter sometimes, "precursor composition" is a hydrated, cohesive gel. A cohesive gel, relative to a non-cohesive gel, is better able retain its shape and resist deformation, for example, after being subjected to shear or other stresses. It has been discovered by the present inventor that such cohesive gels are less likely to substantially degrade or become unstable over time or when subjected to external stimuli such as sterilization, relative to non-cohesive gels.

Without intending to be bound by any particular theory of operability, it is believed that the cohesivity of the precursor composition in some embodiments of the invention acts to substantially or entirely prevent or impede any breakdown or degradation of the crosslinked HA in the composition with the addition of lidocaine.

It is believed that such degradation may primarily occur because many, perhaps most crosslinked HA based gels are conventionally manufactured in a manner that produces gels which are not sufficiently cohesive to prevent such degradation when lidocaine is added. It has now been discovered that the addition of lidocaine to sufficiently cohesive crosslinked HA-based compositions does not cause substantial or significant degradation of the compositions, and the compositions maintain their integrity in terms of rheology, viscosity, appearance and other characteristics even when stored for a lengthy period of time, for example, for a period of time of at least about 6 months, about 9 months, about 12 months, or about 36 months or greater, for example, at ambient temperatures, and even after being subjected to sterilization procedures, for example, autoclaving.

It is a surprising discovery that formulations of crosslinked HA-based compositions including lidocaine can be manufactured in a manner to produce sterilization-stable, injectable HA/lidocaine compositions.

Further described herein is a method for preparing stable HA-based compositions containing an effective amount of lidocaine by preparing a precursor composition, for example, a cohesive, crosslinked HA-based gel, adding lidocaine chlorhydrate to the gel to form a HA/lidocaine gel mixture, and homogenizing the mixture, to obtain a crosslinked HA-based composition that is stable to autoclaving.

In certain embodiments, the precursor composition is a cohesive, hydrated HA-based gel. Such a "cohesive" gel will generally include no greater than between about 1% to about 10% soluble-liquid form or free HA by volume. Such cohesive gels are considered by some in the industry to be monophasic, or substantially single-phase compositions, in that less than about 1% to about 10% of the composition comprises free HA.

In yet other embodiments, the precursor composition is a relatively non-cohesive, hydrated HA-based gel. Such a "non-cohesive" gel generally includes greater than 10%, for example, greater than about 15%, for example, greater than 20% or more of free HA.

In some embodiments, the precursor composition may comprise a first component made up of relatively highly crosslinked HA in a substantially solid phase, and a second component comprising free or relatively less crosslinked HA in a substantially fluidic phase in which the relatively highly crosslinked HA is dispersed.

In some embodiments, the present compositions have a somewhat particulate nature and comprise particles of relatively highly crosslinked HA dispersed in a medium of free HA. In some embodiments, the average size of such particles of crosslinked HA is at least about 200 μm or at least about 250 μm. Such particulate compositions are generally less cohesive than otherwise similar compositions which have no discernable particles, or have particles having an average size of less than 200 μm.

For example, in some embodiments, the precursor composition may be manufactured by pressing a mass of relatively highly crosslinked HA-based gel through a sieve or a mesh to create relatively highly crosslinked HA particles of generally uniform size and shape. These particles are then mixed with a carrier material, for example, an amount of free HA to produce a gel.

In other embodiments, a method of preparing a HA-based composition including an effective amount of lidocaine is provided wherein the method comprises providing a precursor composition including a substantially pH neutral, at least partially crosslinked HA-based gel and adjusting the pH of the gel to a pH of greater than about 7.2, for example, about 7.5 to about 8.0. The method further comprises the step of combining a solution containing lidocaine, for example in the form of lidocaine HCl, with the slightly alkaline gel after the pH has been so adjusted and obtaining a HA-based composition including lidocaine that is stable to autoclaving.

Another method of preparing a stable HA-based composition containing an effective amount of lidocaine, as described elsewhere herein, generally comprises the steps of: providing purified NaHA material, for example, in the form of fibers; hydrating the material; and crosslinking the hydrated material with a suitable crosslinking agent to form a crosslinked HA-based gel. The method further comprises the steps of neutralizing and swelling the gel, and adding to the gel a solution containing lidocaine, preferably an acidic salt of lidocaine chlorhydrate, to form a HA/lidocaine gel. Further still, the method further comprises homogenizing the HA/lidocaine gel and packaging the homogenized HA/lidocaine gel, for example, in syringes for dispensing. The syringes are then sterilized by autoclaving at an effective temperature and pressure. In accordance with the present description, the packaged and sterilized cohesive NaHA/lidocaine gels exhibit enhanced stability relative to HA-based compositions including lidocaine which are made using conventional methods.

The present products and compositions are considered to be sterile when exposed to temperatures of at least about 120° C. to about 130° C. and/or pressures of at least about 12 pounds per square inch (PSI) to about 20 PSI during autoclaving for a period of at least about 1 minute to about 15 minutes.

The present products and compositions also remain stable when stored for long periods of time at room temperature. Preferably, the present compositions remain stable for a period of at least about two months, or at least about six months, or at least about 9 months, or at least about 12 months, or at least about 36 months, at temperatures of at least about 25° C. In a specific embodiment, the compositions are stable at a temperature up to about 45° C. for a period of at least two months.

The manufacturing process includes, in one embodiment, the initial step of providing raw HA material in the form of dry HA fibers or powder. The raw HA material may be HA, its salts and/or mixtures thereof. In a preferred embodiment, the HA material comprises fibers or powder of NaHA, and even more preferably, bacterial-sourced NaHA. In some aspects of the present description, the HA material may be animal derived. The HA material may be a combination of raw materials including HA and at least one other polysaccharide, for example, glycosaminoglycan (GAG).

In some embodiments, the HA material in the compositions nearly entirely comprises or consists of high molecular weight HA. That is, nearly 100% of the HA material in the present compositions may be high molecular weight HA as defined above. In other embodiments, the HA material in the compositions comprises a combination of relatively high molecular weight HA and relatively low molecular weight HA, as defined above.

The HA material of the compositions may comprise between about 5% to about 95% high molecular weight HA with the balance of the HA material including low molecular weight HA. In one embodiment of the invention, the ratio of high molecular weight to low molecular weight HA is at least about, and preferably greater than 2 (w/w≥2) with the high molecular weight HA having a molecular weight of above 1.0 MDa.

It will be appreciated by those of ordinary skill in the art that the selection of high and low molecular weight HA material and their relative percentages or ratios is dependent upon the desired characteristics, for example, extrusion force, elastic modulus, viscous modulus and phase angle expressed as the ratio of viscous modulus to elastic modulus, cohesivity, etc. of the final HA-based product. For additional information that may be helpful in understanding this and other aspects of the present disclosure, see Lebreton, U.S. Patent Application Publication No. 2006/0194758, the entire disclosure of which is incorporated herein by this reference.

The HA-based gels can be prepared according to the present description by first cleaning and purifying dry or raw HA material having a desired high/low molecular weight ratio. These steps generally involve hydrating the dry HA fibers or powder in the desired high/low molecular weight ratio, for example, using pure water, and filtering the material to remove large foreign matters and/or other impurities. The filtered, hydrated material is then dried and purified. The high and low molecular weight HA may be cleaned and purified separately, or may be mixed together, for example, in the desired ratio, just prior to crosslinking.

In one aspect of the present disclosure, pure, dry NaHA fibers are hydrated in an alkaline solution to produce an free NaHA alkaline gel. Any suitable alkaline solution may be used to hydrate the NaHA in this step, for example, but not limited to aqueous solutions containing sodium hydroxide (NaOH), potassium hydroxide (KOH), sodium bicarbonate (NaHCO$_3$), lithium hydroxide (LiOH), and the like. In another embodiment, the suitable alkaline solution is aqueous solutions containing NaOH. The resulting alkaline gel will have a pH above 7.5. The pH of the resulting alkaline gel can have a pH greater than 9, or a pH greater than 10, or a pH greater than 12, or a pH greater than 13.

The next step in the manufacturing process involves the step of crosslinking the hydrated, alkaline NaHA gel with a suitable crosslinking agent. The crosslinking agent may be any agent known to be suitable for crosslinking polysaccharides and their derivatives via their hydroxyl groups. Suitable crosslinking agents include, but are not limited to, 1,4-butanediol diglycidyl ether (or 1,4-bis(2,3-epoxypropoxy)butane or 1,4-bisglycidyloxybutane, all of which are commonly known as BDDE), 1,2-bis(2,3-epoxypropoxy)ethylene and 1-(2,3-epoxypropyl)-2,3-epoxycyclohexane. The use of more than one crosslinking agent or a different crosslinking agent is not excluded from the scope of the present disclosure. In one aspect of the present disclosure, the HA gels described herein are crosslinked using BDDE.

The step of crosslinking may be carried out using any means known to those of ordinary skill in the art. Those skilled in the art appreciate how to optimize conditions of crosslinking according to the nature of the HA, and how to carry out crosslinking to an optimized degree.

Degree of crosslinking for purposes of the present disclosure is defined as the percent weight ratio of the crosslinking agent to HA-monomeric units within the crosslinked portion of the HA based composition. It is measured by the weight ratio of HA monomers to crosslinker (HA monomers: crosslinker).

The degree of crosslinking in the HA component of the present compositions is at least about 2% and is up to about 20%.

In other embodiments, the degree of crosslinking is greater than 5%, for example, is about 6% to about 8%.

In some embodiments, the degree of crosslinking is between about 4% to about 12%. In some embodiments, the degree of crosslinking is less than about 6%, for example, is less than about 5%.

In some embodiments, the HA component is capable of absorbing at least about one time its weight in water. When neutralized and swollen, the crosslinked HA component and water absorbed by the crosslinked HA component is in a weight ratio of about 1:1. The resulting hydrated HA-based gels have a characteristic of being highly cohesive.

The HA-based gels in accordance with some embodiments of the invention may have sufficient cohesivity such that the gels will not undergo substantial phase separation after centrifugation of the gel at 2000 rd/min for 5 minutes. In another embodiment, the gels have the characteristic of being capable of absorbing at least one time their weight of water and have sufficient cohesivity such that when swollen with water at a gel/water weight ratio of about 1:1, the gels maintain their integrity, for example, when subjected to centrifugation.

The hydrated crosslinked, HA gels may be swollen to obtain the desired cohesivity. This step can be accomplished by neutralizing the crosslinked, hydrated HA gel, for example by adding an aqueous solution containing of an acid, such as HCl. The gels are then swelled in a phosphate buffered saline (PBS) solution for a sufficient time and at a low temperature.

In one embodiment, the resulting swollen gels are highly cohesive with no visible distinct particles, for example, no visibly distinct particles when viewed with the naked eye. In one embodiment, the gels have no visibly distinct particles under a magnification of less than 35×.

The cohesive, substantially single-phase gels are now purified by conventional means such as, dialysis or alcohol precipitation, to recover the crosslinked material, to stabilize the pH of the material and to remove any un-reacted crosslinking agent. Additional water or a slightly alkaline aqueous solution can be added to bring the concentration of the NaHA to a desired concentration.

The pH of the purified, substantially pH neutral, crosslinked HA gels are preferably adjusted to cause the gels to become slightly alkaline such that the gels have a pH of greater than about 7.2, for example, about 7.5 to about 8.0. This step may be accomplished by any suitable means, for example, by adding a suitable amount of dilute NaOH, KOH, NaHCO$_3$ or LiOH, to the gels or any other alkaline molecule, solution and/or buffering composition know by one skilled in the art.

An effective amount of lidocaine, such as lidocaine HCl, is then added to the purified cohesive NaHA gels. For example, in some embodiments, the lidocaine HCl is provided in a powder form which is solubilized using water for injection (WFI). The gels are kept neutral with a buffer or by adjustment with diluted NaOH in order that the final HA/lidocaine composition will have a desired, substantially neutral pH. The final HA-based filler compositions including lidocaine have a lidocaine concentration of between at least about 0.1% and about 5%, for example, about 2% w/w of the composition, or in another example about 0.3%.

After the addition of the lidocaine HCl, or alternatively, during the addition of the lidocaine HCl, the HA/lidocaine gels, or compositions, are homogenized to create highly homogenous cohesive HA/lidocaine gels having a desired consistency and stability. The homogenization step may comprise mixing, stirring, or beating the gels with a controlled shearing force to obtain a substantially homogenous mixture.

The HA/lidocaine compositions described herein display a viscosity which is dependent on the composition's properties and the presence of at least one anesthetic agent. The viscosity of the HA/lidocaine compositions can be from about 50 Pa*s to about 450 Pa*s. In other embodiments, the viscosity can be from about 50 Pa*s to about 300 Pa*s, from about 100 Pa*s to about 400 Pa*s, or about 250 Pa*s to about 400 Pa*s, or about 50 Pa*s to about 250 Pa*s.

After homogenization, the HA/lidocaine compositions are introduced into syringes and sterilized. Syringes useful according to the present description include any syringe known in the art capable of delivering viscous dermalfiller compositions. The syringes generally have an internal volume of about 0.4 mL to about 3 mL, more preferably between about 0.5 mL and about 1.5 mL or between about 0.8 mL and about 2.5 mL. This internal volume is associated with an internal diameter of the syringe which plays a key role in the extrusion force needed to inject high viscosity dermalfiller compositions. The internal diameters are generally about 4 mm to about 9 mm, more preferably from about 4.5 mm to about 6.5 mm or from about 4.5 mm to about 8.8 mm. Further, the extrusion force needed to deliver the HA/lidocaine compositions from the syringe is dependent on the needle gauge. The gauges of needles used generally include gauges between about 18 G and about 40 G, more preferably about 25 G to about 33 G or from about 16 G to about 25 G. A person of ordinary skill in the art can determine the correct syringe dimensions and needle gauge required to arrive at a particular extrusion force requirement.

The extrusion forces displayed by the HA/lidocaine compositions described herein using the needle dimensions described above are at an injection speeds that are comfortable to a patient. Comfortable to a patient is used to define a rate of injection that does not injure or cause excess pain to a patient upon injection to the soft tissue. One skilled in the art will appreciate that comfortable as used herein includes not only patient comfort, but also comfort and ability of the physician or medical technician injecting the HA/lidocaine compositions. Although certain extrusion forces may be achievable with the HA/lidocaine compositions of the present description, one skilled in the art understands that high extrusion forces can lead to lack of control during injection and that such lack of control may result in additional pain to the patient. Extrusion forces of the present HA/lidocaine compositions can be from about 8 N to about 15 N, or more preferably from about 10 N to about 13 N, or about 11 N to about 12 N, for example, at an extrusion rate of about 12.5 mm/min.

Sterilization, as used herein comprises any method known in the art to effectively kill or eliminate transmissible agents, preferably without substantially altering of degrading the HA/lidocaine compositions.

One preferable method of sterilization of the filled syringes is by autoclave. Autoclaving can be accomplished by applying a mixture of heat, pressure and moisture to a sample in need of sterilization. Many different sterilization temperatures, pressures and cycle times can be used for this step. For example, the filled syringes may be sterilized at a temperature of at least about 120° C. to about 130° C. or greater. Moisture may or may not be utilized. The pressure applied is in some embodiments depending on the temperature used in the sterilization process. The sterilization cycle may be at least about 1 minute to about 20 minutes or more.

Another method of sterilization incorporates the use of a gaseous species which is known to kill or eliminate transmissible agents. Preferably, ethylene oxide is used as the sterilization gas and is known in the art to be useful in sterilizing medical devices and products.

A further method of sterilization incorporates the use of an irradiation source which is known in the art to kill or eliminate transmissible agents. A beam of irradiation is targeted at the syringe containing the HA/lidocaine solution, and the wavelength of energy kills or eliminates the unwanted transmissible agents. Preferable energy useful include, but is not limited to ultraviolet (UV) light, gamma irradiation, visible light, microwaves, or any other wavelength or band of wavelengths which kills or eliminates the unwanted transmissible agents, preferably without substantially altering of degrading the HA/lidocaine composition.

Further described are In another embodiment, methods of manufacturing cohesive HA-based compositions generally comprising the steps of providing a crosslinked HA-based gel without an anesthetic, (hereinafter, sometimes, a precursor gel) adjusting the pH of the precursor gel to obtain a gel having a pH of between about 7.2 and 8.0, and adding a suitable amount of lidocaine, or other anesthetic agent, to the pH-adjusted gels to obtain cohesive HA-based compositions that include an anesthetic agent. In one embodiment, the precursor gel is a highly cohesive, substantially single phase gel comprising no greater than about 1% to about 10% free HA by volume, for example, no greater than about 10% free HA by volume. In another embodiment, the precursor gel is a relatively less cohesive gel comprising at least 10% to about 20% or more free HA by volume.

Example 1

Method for Testing for Cohesivity of Gel

For purposes of example only and not to be considered as limiting the present invention in any way, the following tests may be performed in order to evidence or quantify cohesivity of a HA-based gel composition.

First, 0.2 g or 0.4 g of a gel composition to be tested is placed in a glass syringe. Next, 0.2 g or more of phosphate buffer is added to the syringe and the mixture is thoroughly mixed for about 1 hour to obtain a homogenous mixture. Then, the homogenized mixture is centrifuged for 5 min at 2000 tr/min to remove the air bubbles and to allow the decantation of any particles. The syringe is then held in a vertical position and one drop of eosin colorant is deposited at the surface of the gel by means of a syringe and an 18 G needle. After 10 min, the dye has slowly diffused through the gel.

After dilution of the gel, homogenization and decantation, a relatively low cohesivity gel shows a phase separation (an upper diluted less viscous phase without particles and a lower one composed of decanted particles that are visible with the naked eye or under microscope). Under the same conditions, a highly cohesive gel shows substantially no phase separation, and the dye is prevented from diffusing into the cohesive formulation. A relatively less cohesive gel, on the other hand, shows a clear phase separation.

Example 2

Synthesis of a Soft Tissue Filler with Lidocaine

NaHA fibers or powder are hydrated in an alkaline solution, for example, an aqueous solution containing NaOH. The mixture is mixed at ambient temperature, about 23° C., to form a substantially homogenous, alkaline HA gel.

A crosslinking agent, BDDE, is diluted in an aqueous solution and added to the alkaline HA gel. The mixture is homogenized for several minutes.

Alternatively, BDDE can be added directly to the HA fibers (dry state) at the beginning of the process, prior to the hydration. The crosslinking reaction will then start relatively slowly at ambient temperature, ensuring even better homogeneity and efficacy of the crosslinking. Methods of crosslinking polymers in the dry state using a polyfunctional crosslinking agent such as BDDE are described in, for example, Piron et al., U.S. Pat. No. 6,921,819 which is incorporated herein by reference in its entirety as if it were part of the present specification.

The resulting crosslinked HA gel mixture is then heated at about 50° C. for about 2.5 hours. The material is now a highly crosslinked HA/BDDE gel (aspect=solid gel). This crosslinked gel is then neutralized with a suitable acidic solution. The neutralized HA gel is then swollen in a phosphate buffer at a cold temperature, for example a temperature of about 5° C., to obtain a highly cohesive HA gel. In this specific example, the phosphate buffered saline solution contains water-for-injection (WFI), disodium hydrogen phosphate, and sodium dihydrogen phosphate. When neutralized and swollen, the crosslinked HA component and water absorbed by the crosslinked HA component is in a weight ratio of about 1:1.

The cohesive swollen HA gel is then mechanically stirred and filled into dialysis membranes and dialyzed against a phosphate buffer. The HA gel is then filled into dialysis membranes and dialyzed against a phosphate buffer for up to several days with regular changes of the bath, in order to remove the un-reacted crosslinker, to stabilize the pH close to neutrality (pH=7.2) and to ensure proper osmolarity of the HA gel. The osmolarity of the resulting cohesive HA gel is between about 200 mOsmol and about 400 mOsmol, most preferably about 300 mOsmol.

After dialysis, the resulting cohesive HA gel has a substantially neutral pH, preferably about 7.2, and no visibly distinct particles in a fluidic media when viewed at a magnification of less than about 35×.

Lidocaine chlorhydrate (lidocaine HCl) in powder form is first solubilized in WFI and filtered through a 0.2 μm filter. Dilute NaOH solution is added to the cohesive HA gel in order to reach a slightly basic pH (for example, a pH of between about 7.5 and about 8). The lidocaine HCl solution is then added to the slightly basic gel to reach a final desired concentration, for example, a concentration of about 0.3% (w/w). The resulting pH of the HA/lidocaine mixture is then about 7 and the HA concentration is about 24 mg/mL. Mechanical mixing is performed in order to obtain a proper homogeneity in a standard reactor equipped with an appropriate blender mechanism. The resulting composition is cohesive.

If desired, a suitable amount of free HA gel may be added to the HA/lidocaine gel mixture with the advantage of increasing the kinetics of lidocaine delivery. For example, free HA fibers are swollen in a phosphate buffer solution, in order to obtain a homogeneous viscoelastic gel. This free HA gel is then added to the crosslinked HA/lidocaine gel (for example, at about 5%, w/w). The resulting gel is then filled into sterile syringes and autoclaved at sufficient temperatures and pressures for sterilization for at least about 1 minute.

After autoclaving, the final HA/lidocaine product is packaged and distributed to physicians. The product manufactured in accordance with this method exhibits one or more characteristics of stability as defined elsewhere herein. For example, the autoclaved HA/lidocaine product has a viscosity, cohesivity, and extrusion force that are acceptable. No degradation of the HA/lidocaine gel product is found during testing of the product after the product has spent several months in storage.

Example 3

Properties of Soft Tissue Fillers

Properties of HA/lidocaine compositions manufactured in accordance with methods described herein are shown in the Table 1 below. Extrusion force for example was measured using an INSTRON® Advanced Materials Testing System Model 5564 (Instron, Norwood, Mass.) running BLUE-HILL® software version 2.11 (Instron, Norwood, Mass.). Other rheological data was collected using a Versa test Column with a MECMESIN® dynamometer AGF 100 N (Mecmesin Limited, West Sussex, United Kingdom) running Emperor software and a THERMO FISHER SCIENTIFIC® Rheometer RS600 (Thermo Fisher Scientific, Inc. Corp., Waltham, Mass.).

TABLE 1

| | HA/lidocaine Composition |
|---|---|
| Appearance | Homogeneous transparent gel |
| pH | 7.2 |
| Extrusion force (N) | 10.8N |

TABLE 1-continued

| | HA/lidocaine Composition |
|---|---|
| NaHA Content | 23.7 mg/g |
| Sterility | Sterile (SAL ≤ $10^{-6}$) |
| Osmolarity | 321 mOsml/kg |
| Lidocaine Content (%) | 0.29% |
| 2,6-dimethylaniline content | Conforms |

In order to ensure that product specifications were maintained throughout the shelf life of the composition, multiple studies were performed. In addition, 2,6-dimethylaniline content was measured in order to confirm the absence of lidocaine degradation.

Table 2 provides a summary of stability testing results on the composition manufactured as described herein.

TABLE 2

| | HA/lidocaine Composition | | |
|---|---|---|---|
| Test | 3 month results | 6 month results | 9 month results |
| Aspect Transparent and homogeneous | Conforms | Conforms | Conforms |
| pH | 7.2 | 7.2 | 7.2 |
| Extrusion Force (N) | 11.9 | 11.1 | 11.9 |
| NaHA Concentration (mg/g) | 23.8 | 23.1 | 24.2 |
| Sterility | Conforms | Conforms | Conforms |
| Osmolarity (mOsm/kg) | 349 | 329 | 342 |
| Lidocaine Content (%) | 0.29 | 0.29 | 0.29 |
| 2,6-dimethylaniline content | Conforms | Conforms | Conforms |

It was discovered that at 9 months' time (from manufacture date), the composition continues to meet the product specifications.

Example 4

Stability of Soft Tissue Fillers

The following sterilized HA formulations (Samples 1-6) were obtained for testing.

Sample 1 is a free HA mixture 13.5 mg/g, with hydroxyl propyl methyl cellulose (HPMC) 5.5 mg/g.

Sample 2 is contains 5.5-6.5 mg/mL of high molecular weight HA (about 4-6 MDa) and a degree of elasticity (G') of about 200.

Sample 3 is a non-commercial gel made of distinct gel particles mixed with free HA (80/20, w/w). The HA particles (80%) is obtained by disintegration of a "solid" heavily crosslinked HA gel. The particles have different shapes and dimensions (several microns to several mm).

Sample 4 is a cohesive crosslinked HA formulation. Sample 4 has a HA concentration of about 18 mg/mL, less than 6% crosslinking, a G' of about 60 and a high molecular weight to low molecular weight HA ratio from about 95% to about 5%, to about 100% high molecular weight HA.

Sample 5 is a cohesive crosslinked HA formulation. Sample 5 has a HA concentration of about 24 mg/mL, about 6% crosslinking, a G' of about 170 and a high molecular weight to low molecular weight HA ratio from about 95% to 5% to about 100% high molecular weight HA.

Sample 6 is a cohesive crosslinked HA formulation. Sample 6 has a HA concentration of about 20 mg/mL, about 5% crosslinking, a G' of about 450 and a high molecular weight to low molecular weight HA ratio from about 10% to 90%.

Each of Samples 1-6 was prepared as follows:

Test 1: About 20 g of each of Samples 1-6 was individually mixed with a solution of lidocaine chlorhydrate and homogenized. In this test, during the addition of the lidocaine chlorhydrate, the pH of the sample gel is substantially neutral and is not adjusted, for example, with the addition of sodium hydroxide solution. Each of the Samples was then filled into syringes and autoclaved.

Test 2: About 20 g of each of Samples 1-6 was individually mixed with a solution of lidocaine chlorhydrate, and the pH was adjusted to 7.2 using NaOH solution as described in Example 2 above. Each of the Samples was then filled into syringes and autoclaved.

Test 3: About 20 g of each of Samples 1-6 was mixed with an equivalent amount of WFI to take into account dilution effect. No lidocaine was added. Each of the Samples was then filled into syringes and autoclaved.

Results: For each of the Samples in Tests 1-3, rheological measurements were performed using the rheological measurement equipment described in Example 3. The results are generally shown graphically in accompanying FIGS. 1-8. Definitions of symbols and units in Table 3 generally apply to FIGS. 1-8.

TABLE 3

| Symbol | Name | Units | Description |
|---|---|---|---|
| G' | Elastic Modulus | Pa | Quantifies the solid-like behavior or resistance to permanent deformation. |
| G" | Viscous Modulus | Pa | Quantifies the liquid-like behavior or resistance to flow. |
| (G"/G') | Tan Delta | | (G"/G') the ratio of the viscous modulus to the elastic modulus and useful for quantifying the extent of elasticity. A value is below 1 means that the fluid is more elastic conversely a value above 1 means the fluid is more viscous. |

As a general guideline, a stable Sample including lidocaine prepared according to Test 1 or 2 would exhibit similar viscosity, when subjected to shear across a range of frequencies, as the Samples prepared according to Test 3 which contain no lidocaine.

Figure 2:
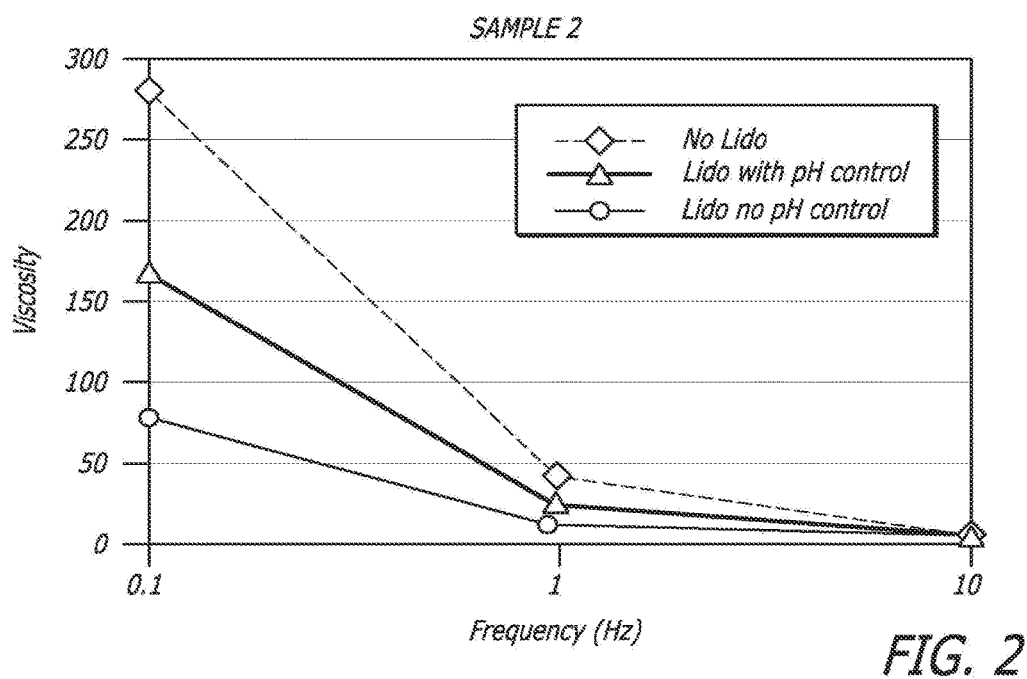
FIG. 2 graphically illustrates the viscosity of Sample 2 prepared without lidocaine, with lidocaine and pH adjustment during formation and with lidocaine but without pH adjustment during formation versus the shear frequency.

It was discovered that neither of Samples 1 and 2 with lidocaine was stable to autoclaving and as a result, degrade and become substantially less viscous in both Test 1 and Test 2. FIGS. 1 and 2 in particular illustrate that Samples 1 and 2 have a lowered viscosity, and hence were less stable to sheer when the product was prepared with lidocaine as compared to the product without lidocaine, even when the Sample was prepared according to Test 2 wherein a pH adjustment was performed.

Figure 3:
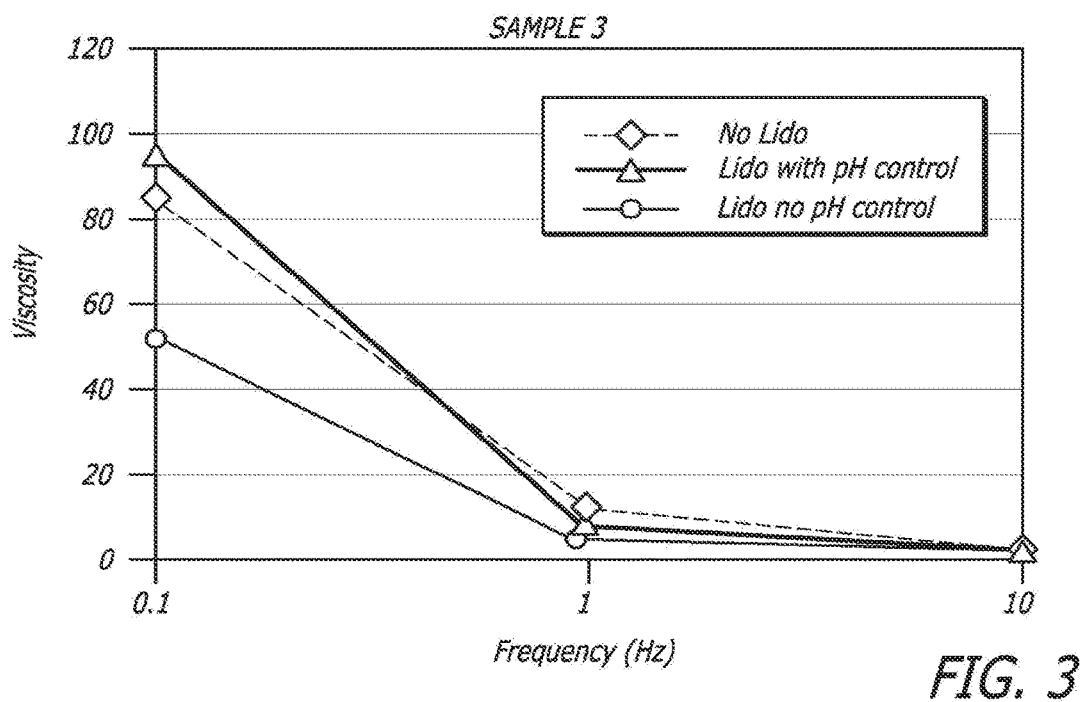
FIG. 3 graphically illustrates the viscosity of Sample 3 prepared without lidocaine, with lidocaine and pH adjustment during formation and with lidocaine but without pH adjustment during formation versus the shear frequency.
Figure 4:
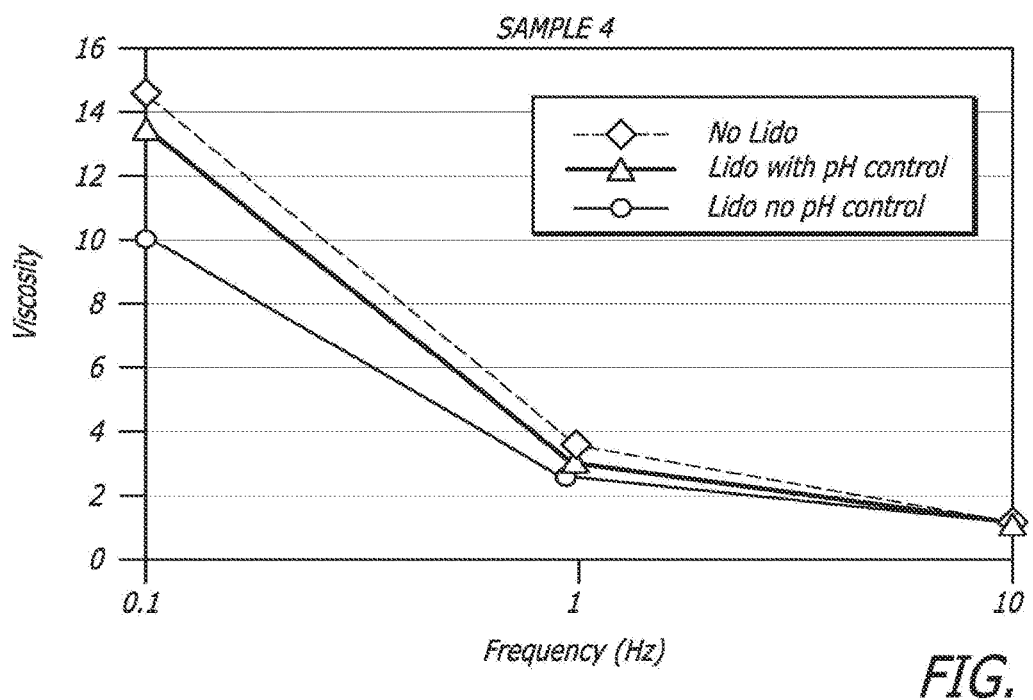
FIG. 4 graphically illustrates the viscosity of Sample 4 prepared without lidocaine, with lidocaine and pH adjustment during formation and with lidocaine but without pH adjustment during formation versus the shear frequency.
Figure 6:
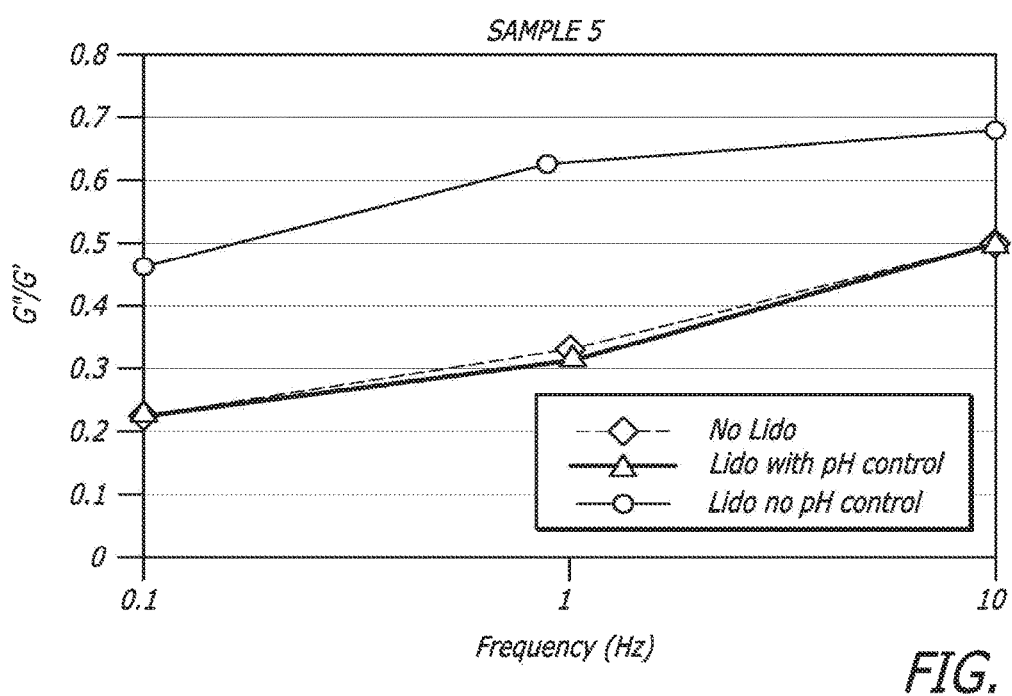
FIG. 6 graphically illustrates the relative viscosity/elasticity characteristics of Sample 5 prepared without lidocaine, with lidocaine and pH adjustment during formation and with lidocaine but without pH adjustment during formation versus the shear frequency.
Figure 7:
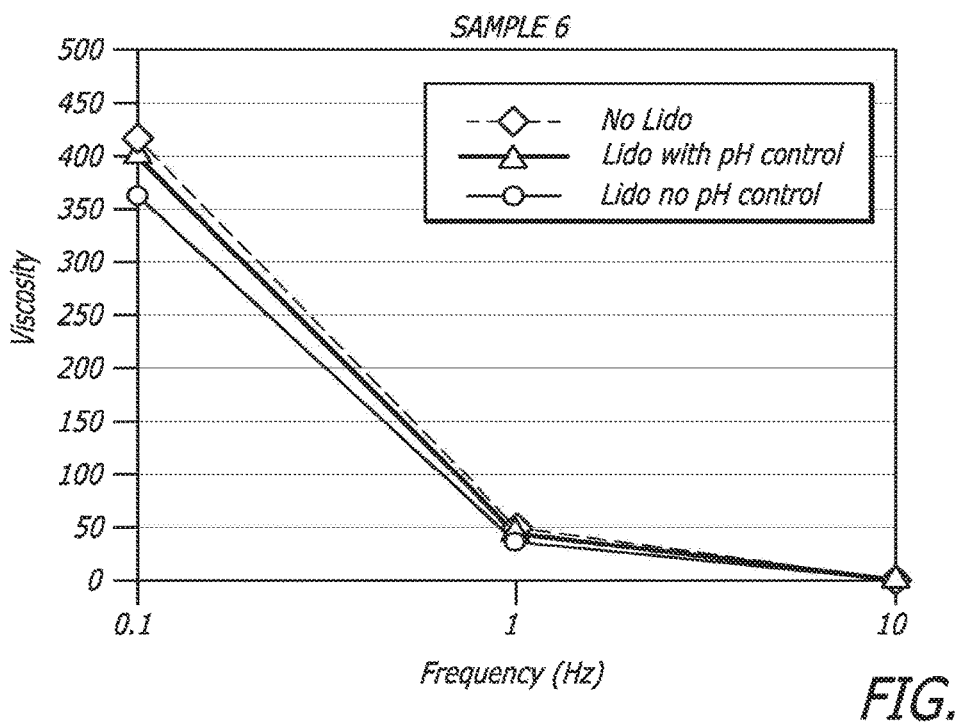
FIG. 7 graphically illustrates the viscosity of Sample 6 prepared without lidocaine, with lidocaine and pH adjustment during formation and with lidocaine but without pH adjustment during formation versus the shear frequency.
Figure 8:
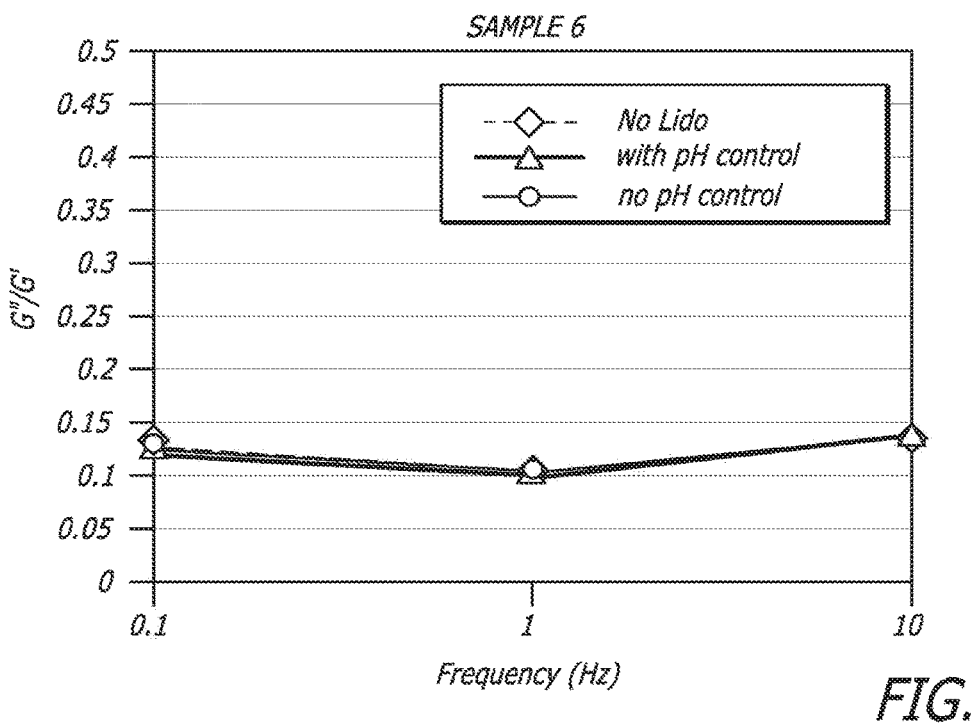
FIG. 8 graphically illustrates the relative viscosity/elasticity characteristics of Sample 6 prepared without lidocaine, with lidocaine and pH adjustment during formation and with lidocaine but without pH adjustment during formation versus the shear frequency.

With regard to viscosity, Sample 3 and Sample 4 were found to be stable to autoclaving in Test 2 but were not stable in Test 1. Sample 6 was found to be stable to autoclaving in both Test 1 and Test 2. FIGS. 3 and 4 illustrate that Samples 3 and 4 were stable when prepared with lidocaine and with pH adjustment, but were not stable when lidocaine was added and the pH not adjusted. FIG. 6 illustrates that Sample 5 prepared with lidocaine and pH control had similar viscous and elastic properties (G"/G') to Sample 5 prepared without lidocaine. When Sample 5 was prepared with lidocaine and no pH adjustment, the viscous and elastic properties changed an insubstantial amount (FIG. 6). FIGS. 7 and 8 illustrate that Sample 6 was stable and had similar viscous and elastic properties (G"/G') when prepared with lidocaine, both with and without pH control.

Figure 5:
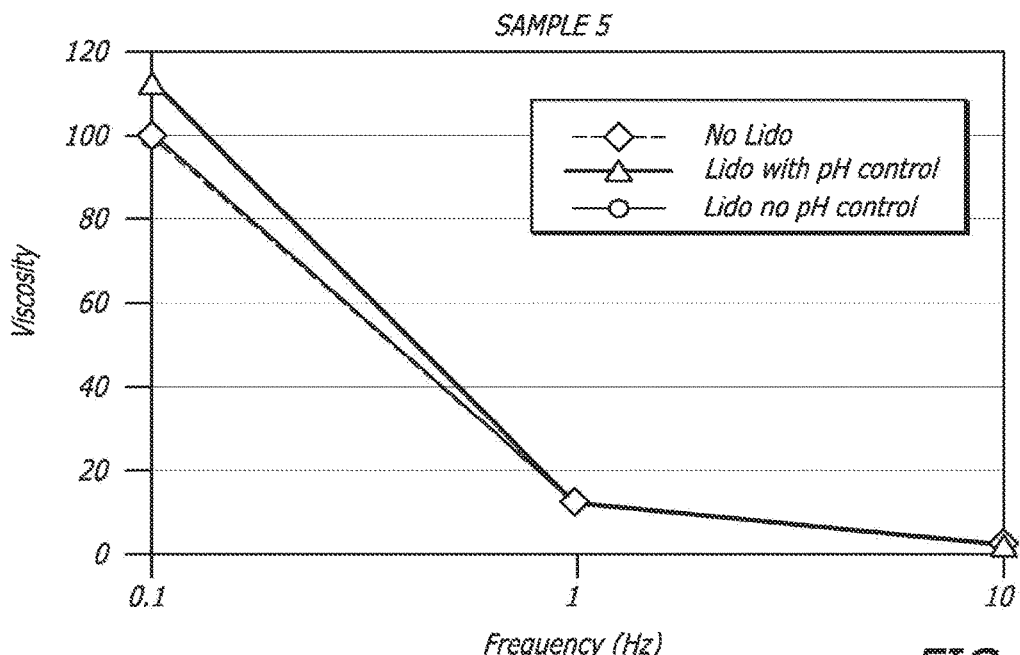
FIG. 5 graphically illustrates the viscosity of Sample 5 prepared without lidocaine, with lidocaine and pH adjustment during formation and with lidocaine but without pH adjustment during formation versus the shear frequency.

FIGS. 1-5 and 7 show changes in viscosity between the autoclaved Samples without lidocaine ("No Lido") and the autoclaved Samples with lidocaine ("Lido no pH control"). More specifically, as shown in FIGS. 1-3, the viscosity at 0.1 Hz of Samples 1, 2 and 3 decreased at least about 35% when lidocaine was added. As shown in FIGS. 4, 5 and 7, the viscosity at 0.1 Hz of cohesive Samples 4, 5 and 6, in accordance with the invention, did not decrease to any appreciable extent (not greater than about 30%) when lidocaine was added and the combination was autoclaved.

Sample 6 was found to be stable to autoclaving in both of Test 1 and Test 2. FIG. 7 illustrates that Sample 6, no matter how it is produced, had similar viscosity and hence little shear comparison between preparation protocols. FIG. 8 further illustrates that Sample 6 retained similar viscous and elastic properties no matter how it was produced.

Example 5

Kinetic Release

The following example illustrates the kinetic of release of lidocaine from cohesive HA gels according to the present description. The aim of the Example is to show that the lidocaine contained in cohesive HA gels according to the present description is freely released from the gels when placed in the skin.

Dialysis was performed for different periods of time (about 10 g of gel were placed in a small dialysis bag and then put in 30 g of water). After each dialysis was stopped at a given time, the gel was homogenized with a spatula and the amount of lidocaine was determined by UV method. The final concentration of the dialysis bath met the theoretical concentration of lidocaine which indicates the free release of lidocaine from the gel.

Figure 9:
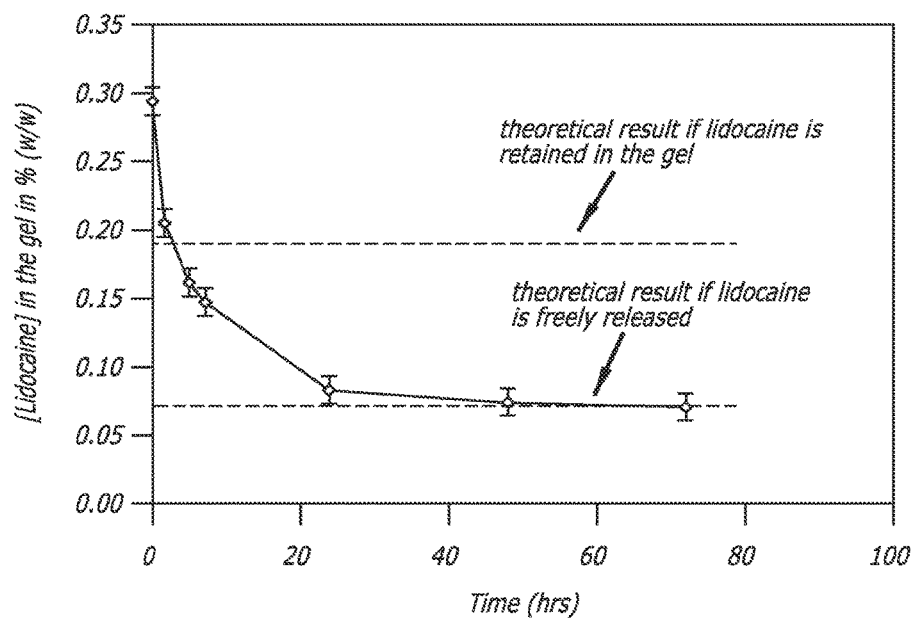
FIG. 9 graphically illustrates the lidocaine concentration in the gel from Sample 5 in Example 4 made by the procedure of Test 2 versus time.

Table 3 illustrates lidocaine concentration in % (w/w), correction of the value and determination of the % of released lidocaine. Additionally, FIG. 9 graphically illustrates the results tabulated in Table 4 below. Within FIG. 9 is indicated the theoretical equilibrium concentration of lidocaine that would exist if the lidocaine were retained in the gel or if it were to be freely released. As is graphically illustrated therein, the data suggest that the lidocaine is freely released from the gel.

TABLE 4

|  | MMA3056 | MMA4031-EC6 | MMA4031-EC2 | MMA4031-EC3 | MMA4031-EC4 | MMA4031-EC5 | MMA4029-EC7 |
|---|---|---|---|---|---|---|---|
| Dialysis time (h) | 0 hr | 1 hr 30 min | 5 hr | 7 hr | 23 hr | 48 hr | 72 hr |
| [lidocaine] (%) | 0.29 | 0.20 | 0.16 | 0.15 | 0.08 | 0.07 | 0.07 |

The concentration profile of lidocaine in Sample 5 from Example 4 (FIG. 9) shows that over time it reaches an equilibrium that corresponds to free release of lidocaine. This in vitro study shows that lidocaine is freely released from the gel and not retained in the gel once implanted.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A dermal filler comprising:
    hyaluronic acid (HA) crosslinked with 1,4 butanediol diglycidyl ether (BDDE), and
    lidocaine;
    wherein the lidocaine is freely released in vivo;
    wherein the dermal filler is sterile; and
    wherein the dermal filler is made by a process comprising:
        crosslinking HA with BDDE to obtain a crosslinked HA composition;
        adding lidocaine to the crosslinked HA composition; and
        heat sterilizing the crosslinked HA composition with added lidocaine to obtain a sterile dermal filler.

2. The dermal filler of claim 1, wherein the process further comprises adjusting the pH of the crosslinked HA composition to obtain an alkaline crosslinked HA composition.

3. The dermal filler of claim 2, wherein the pH adjustment is performed before adding the lidocaine.

4. The dermal filler of claim 2, wherein the pH adjustment comprises adjusting the pH to about 7.5 to about 8.0.

5. The dermal filler of claim 2, wherein the pH adjustment comprises adjusting the pH to above about 7.5.

6. The dermal filler of claim 1, wherein the adding the lidocaine comprises adding a solution containing lidocaine HCl.

7. The dermal filler of claim 1, wherein the process further comprises passing the crosslinked HA composition through a sieve before adding the lidocaine.

8. The dermal filler of claim 7, wherein the process further comprises adding free HA gel to the crosslinked HA composition after the crosslinked HA composition has been passed through the sieve.

9. The dermal filler of claim 7, wherein the crosslinked HA composition, after being passed through the sieve, comprises particles of crosslinked HA having an average particle size of at least about 200 μm.

10. The dermal filler of claim 7, wherein the crosslinked HA composition, after being passed through the sieve, comprises particles of crosslinked HA having an average particle size of at least about 250 μm.

11. The dermal filler of claim 7, wherein the crosslinked HA composition, after being passed through the sieve, comprises particles of crosslinked HA having an average particle size of less than about 200 μm.

12. The dermal filler of claim 1, wherein the process further comprises homogenizing the crosslinked HA composition before adding the lidocaine.

13. The dermal filler of claim 1, wherein the dermal filler has a lidocaine concentration of between about 0.1% and about 5.0% w/w.

14. The dermal filler of claim 1, wherein the dermal filler has a HA concentration between about 20 mg/mL and about 30 mg/mL.

15. The dermal filler of claim 1, having a lidocaine concentration of 0.3% w/w and a HA concentration between about 20 mg/mL and about 30 mg/mL.

16. A dermal filler composition comprising:
    a composition comprising hyaluronic acid (HA) crosslinked with 1,4 butanediol diglycidyl ether (BDDE), wherein the HA is not crosslinked to a non-HA biopolymer, and lidocaine;
    wherein the dermal filler is made by a process comprising:
        crosslinking HA with BDDE to obtain a crosslinked HA;
        adding lidocaine to the crosslinked HA; and
        heat sterilizing the crosslinked HA with added lidocaine to obtain a sterile dermal filler.

17. The dermal filler of claim 16, wherein the process further comprises adjusting the pH of the crosslinked HA to obtain an alkaline crosslinked HA.

18. The dermal filler of claim 17, wherein the adjusting the pH is performed before adding the lidocaine.

19. The dermal filler of claim 16, wherein adding the lidocaine comprises adding a solution containing lidocaine HCl.

20. The dermal filler of claim 16, wherein the crosslinked HA comprises particles of crosslinked HA having an average particle size of at least about 200 μm.

21. The dermal filler of claim 16, wherein the crosslinked HA comprises particles of crosslinked HA having an average particle size of less than about 200 μm.

22. The dermal filler of claim 16, wherein the dermal filler has a lidocaine concentration of between about 0.1% and about 5.0% w/w.

23. The dermal filler of claim 16, wherein the dermal filler has a HA concentration of between about 20 mg/mL and about 30 mg/mL.

24. A dermal filler composition comprising:
    a hyaluronic acid (HA) crosslinked with 1,4 butanediol diglycidyl ether (BDDE), and about 0.3% lidocaine by weight, wherein the lidocaine is freely released in vivo and wherein the composition is sterile;
    wherein the composition is made by a process comprising:

crosslinking HA with BDDE to obtain a crosslinked HA;
adding a free HA gel to the crosslinked HA;
adding a solution of lidocaine HCl to the crosslinked HA; and
autoclaving the crosslinked HA having free HA gel and lidocaine HCl added thereto, to obtain a sterile dermal filler composition.

25. A dermal filler product comprising:
a dermal filler composition comprising a hyaluronic acid (HA) crosslinked with 1,4 butanediol diglycidyl ether (BDDE), and between about 0.1% to about 5.0% lidocaine by weight, wherein the HA is not crosslinked to a non-HA biopolymer, and wherein the composition is sterile;
a syringe containing the sterile composition;
wherein the product is made by a process comprising:
crosslinking HA with BDDE to obtain a crosslinked HA;
adding lidocaine to the crosslinked HA to obtain a crosslinked HA containing lidocaine; and
packaging the crosslinked HA containing lidocaine in a syringe; and
autoclaving the syringe containing the crosslinked HA containing lidocaine to obtain a dermal filler product.

26. The dermal filler product of claim 25, wherein the sterile composition contained in the syringe has a volume between about 0.8 mL and about 2.5 mL.

27. The dermal filler product of claim 25, wherein the sterile composition has a HA concentration of about 20 mg/mL to about 30 mg/mL.

28. The dermal filler product of claim 25, wherein the sterile composition is stable at ambient temperature for at least about 6 months.

29. The dermal filler product of claim 25, wherein the sterile composition comprises particles of crosslinked HA having an average particle size of at least about 200 µm.

30. The dermal filler product of claim 25, wherein the sterile composition comprises particles of crosslinked HA having an average particle size of less than about 200 µm.

* * * * *